(12) United States Patent
Akhter et al.

(10) Patent No.: US 6,602,493 B2
(45) Date of Patent: Aug. 5, 2003

(54) HAIR RELAXER SYSTEM AND METHOD THEREFOR

(75) Inventors: Humayoun Akhter, Hinsdale, IL (US); Ali N. Syed, Inverness, IL (US)

(73) Assignee: Avlon Industries, Inc., Bedford Park, IL (US)

( * ) Notice: Subject to any disclaimer, the term of this patent is extended or adjusted under 35 U.S.C. 154(b) by 30 days.

(21) Appl. No.: 09/783,904

(22) Filed: Feb. 15, 2001

(65) Prior Publication Data

US 2003/0049222 A1 Mar. 13, 2003

(51) Int. Cl.$^7$ .............................. A61K 7/06; A61K 7/09; A01N 25/34
(52) U.S. Cl. .................... 424/70.1; 424/70.2; 424/70.4; 424/402
(58) Field of Search ................................ 424/70.2, 70.4

(56) References Cited

U.S. PATENT DOCUMENTS

| | | | |
|---|---|---|---|
| 4,581,229 A | | 4/1986 | Petrow ........................ 424/70 |
| 5,254,336 A | * | 10/1993 | Hoshowski et al. ......... 132/202 |
| 5,293,885 A | * | 3/1994 | Darkwa et al. ............. 132/203 |
| 5,635,167 A | * | 6/1997 | Said et al. .................. 132/202 |

FOREIGN PATENT DOCUMENTS

| WO | WO 93/11737 | * | 6/1993 |
|---|---|---|---|

OTHER PUBLICATIONS

Harry (Ed.), *Harry's Cosmeticology*, 6th Ed., Ch.24 pp 354–356, Chemical Publishing Co., Inc. New York, NY (1973).
Hilderbrand et al., "Trace–Element Analysis in Hair: An Evaluation," *Clin. Chem.*, 20(2), pp148–151 (1974).
Assarian et al., "Effect of Washing Procedures on Trace–Element Content of Hair," *Clin. Chem.*, 23(9), pp 1771–1772 (1977).
Nordlund MD et al., "On the Cause of Green Hair," *Arch. Dermatol.*, 113, p1700 (1977).
McKenzie PhD., "Alteration of the zinc and copper concentration of hair," *Amer. J. of Clinical Nutrition*, 31, pp 470–476 (Mar. 1978).
Bhat et al., "The green hair problem: a preliminary investigation," *J.Soc.Cosmet. Chem.*, 30, pp 1–8 (1979).
Buckley et al., "Radioisotopic studies concerning the efficacy of standard washing procedures for the cleansing of hair before zinc analysis," *Amer. J. of Clin. Nutrition*, 40, pp 840–846 (Oct. 1984).
Wilhem et al., "Uptake of Aluminum, Cadmium, Copper, Lead, and Zinc by Human Scalp Hair and Elution of the Adsorbed Metals," 13, pp 17–21 (Jan./Feb. 1989).
*After Calcium*, Request Products, Orlando, Florida (undated).
*The Clean Canvas System*, L'Avantgarde, Inc., Simi Valley, California (undated).
*Senscience*, Product label, Senscience International Dist., Division Zotos Corporation, Darien, CT. ©1995.

\* cited by examiner

*Primary Examiner*—Thurman K. Page
*Assistant Examiner*—Isis Ghali
(74) *Attorney, Agent, or Firm*—Olson & Hierl, Ltd.

(57) ABSTRACT

This invention describes a hair relaxer system and method that ameliorates and inhibits the adsorption and retention by alkaline, chemically-relaxed hair of exogenous multivalent metal ion present in the chemical relaxer, in the rinse water or both employed during the process of relaxing naturally curly hair with compositions containing strong chemical base. In a preferred relaxer method aspect, the alkaline, chemically relaxed hair was contacted with an aqueous metal ion chelating composition containing at least one multivalent metal ion chelating agent employing a disclosed delivery system adapted for practical salon use. In another preferred relaxer method embodiment, wipes impregnated with multivalent metal ion chelating composition were employed during the relaxer process.

35 Claims, 1 Drawing Sheet

HAIR RELAXER SYSTEM AND METHOD THEREFOR

TECHNICAL FIELD OF THE INVENTION

This invention relates to the relaxing or straightening of naturally curly hair with strong chemical base and, in particular, to a hair relaxer system and method that ameliorates or inhibits the deposition of exogenous, multivalent metal ion on alkaline, chemically-relaxed hair.

BACKGROUND OF THE INVENTION

Multivalent metal ions, especially alkaline earth metal cations of calcium and magnesium, when present in the water employed for rinsing the hair during cosmetic hair treatments, such as chemical relaxing, permanent waving of hair and even shampooing, can react with anionic constituents in or on the hair to form water insoluble compounds that undesirably adhere to the hair.

Typically, in the salon or in the home, the source of the rinse water is tap water supplied by the local municipality, and in some instances from limestone wells. In some large metropolitan regions, the hardness of the water contains sufficient calcium, magnesium and other minerals to interfere with cosmetic treatments of human hair.

The adsorption and retention of exogenous, multivalent metal ion minerals on hair can be undesirable because the deposited mineral can visually dull the appearance of the hair, make the tactile and handling characteristics of the hair heavy, coated, and difficult to style, and increase its resistance to or interfere with the effectiveness of certain hair treatments, such as dyeing, bleaching, permanent waving, chemical relaxation or straightening, shampooing, conditioning and the like.

Aside from endogenous trace minerals found in hair and exogenous minerals sorbed from rinse water, exogenous mineral deposits in human hair can also come from cosmetic treatments, topical medications, and environmental pollutants. For example, strong chemical bases are typically employed for chemical hair relaxation at a pH of greater than about 12. Such chemical base treatment can leave numerous negatively charged moieties in the hair, thereby making the chemically-relaxed hair more receptive to adsorption and retention of various multivalent metal ions, especially alkaline earth metal cations, present in the rinse water contacting it immediately following such highly alkaline processing. Mineral deposits can build up on the hair surface undesirably and be further exacerbated by employing hard water rinses during the process of chemically relaxing naturally curly hair especially with "no-lye" type hair relaxer compositions.

Commercial chemical hair relaxer products, commonly called "no-lye" relaxers, are two-component products that are mixed together just before use to form the strong organic base, guanidinium hydroxide, in situ. One of the two components typically is an activator solution containing guanidine carbonate and the other component is an emulsion creme containing calcium hydroxide in excess of the stoichiometric amount needed to form the strong base. As a result, the admixture contains the byproduct calcium carbonate, and unreacted calcium hydroxide, each of which can form an observable deposit of calcium mineral on the surface of the hair.

Salon practitioners frequently complain about the mineral buildup on chemically-relaxed hair, because it can interfere with the effectiveness of post-relaxer conditioners, hair coloring, and subsequent chemical relaxing hair treatments. Moreover, mineral buildup on the hair generally also dulls the natural sheen of the hair, makes it hard to comb and style, and leaves the scalp and hair feeling dry and rough. Removal of mineral deposit from chemically-relaxed hair presents problems because, following exposure to strong chemical base, the scalp can be vulnerable to irritation and the chemically relaxed hair can be susceptible to weakening damage thereby limiting aggressive removal of mineral ion deposit.

In some prior attempts at resolving the mineral buildup problem, practitioners have resorted to using chemical pre-treatment products, sometimes called "clarifiers" or "primers" in the trade, to remove mineral buildup from the hair. These commercial products are available and employed in the form of lotions, shampoos or pre-shampoo sprays, which are applied, sometimes with heat, to the hair before the desired subsequent hair product can be used. However, such chemical pre-treatments, and shampoos in particular, are unsuitable for use just before a chemical relaxation procedure, because they undesirably increase the risk of predisposing the scalp to burning or irritation from the strong chemical base during the subsequent chemical relaxation process.

From industry experience, no-lye type hair relaxers are generally regarded as having a low scalp irritation potential, which has accounted for their popularity and success. However, the increased mineral buildup problem observed with no-lye type hair relaxers has caused salon practitioners, in particular, to avoid using this type of hair relaxer in favor of relaxers containing inorganic caustic base, particularly sodium hydroxide (so-called lye-type relaxers), which tend to have a higher scalp irritation potential, in the belief that mineral buildup would not occur. We have now surprisingly discovered that even when inorganic caustic base containing relaxers are employed, alkaline earth metal minerals, and other multivalent metal ions, when present in the rinse water, also deposit on the chemically relaxed hair during the relaxation process.

Thus, there is an ongoing need to resolve the problem of adsorption and retention by chemically relaxed hair of exogenous multivalent metal ions, and of alkaline earth metal ion, in particular. The hair relaxing system and method of this invention provides a resolution to this problem.

SUMMARY OF THE INVENTION

The present invention provides a hair relaxing system and method that ameliorates and inhibits the adsorption and retention by alkaline, chemically-relaxed hair of undesirable exogenous multivalent metal ion present in the chemical relaxer, rinse water or both during the process of relaxing naturally curly hair with compositions having a pH above about 12 containing a hair-relaxing amount of strong chemical base.

In a preferred method aspect, the deposition of exogenous, multivalent metal ion, and calcium and magnesium ion in particular, on alkaline chemically relaxed hair was surprisingly ameliorated and inhibited during the relaxer process by (a) contacting naturally curly hair with a hair relaxing composition having a pH above about pH 12 for a period sufficient to relax all or a portion of the natural curl and then (b) removing the chemical relaxer composition from the alkaline, chemically-relaxed hair employing an aqueous composition having a physiologically tolerable pH and containing an effective chelating amount of at least one exogenous multivalent metal ion chelating agent. It was surprisingly found that concurrently removing the relaxer and contacting alkaline, chemically relaxed hair with the metal ion chelating composition in step (b) for at least about two minutes effectively ameliorated and inhibited sorption and retention of a selected exogenous multivalent metal ion, such that the total content of that metal ion initially present in the hair before the chemical relaxer process was not increased or, increase, if any, was not more than 1.3 fold.

In a particularly preferred method aspect, the foregoing step (b) was carried out during the relaxer process by employing an inventive delivery system adapted for practical salon use. The inventive delivery system beneficially delivers a controlled amount of the metal ion chelating composition concurrently with the rinse water. The beneficial inhibitory effect on metal ion retention is further enhanced by employing soft water preferably having a hardness of not more than 1 ppm. Further the delivery system can be employed under practical salon conditions.

Surprisingly, the adsorption and retention of calcium ion, in particular, by alkaline, chemically-relaxed hair was found to be substantially ameliorated and inhibited by rinsing with an aqueous composition containing not more than about 0.5 weight percent total alkaline earth metal chelating agent employing the inventive delivery system.

In another preferred method aspect, the adsorption and retention of metal ion deposit on alkaline, chemically-relaxed hair was also ameliorated and inhibited in step (b) by (i) removing the chemical relaxer from the hair by rinsing with soft water and then (ii) substantially immediately contacting the water rinsed alkaline, chemically-relaxed hair with a wet wipe impregnated with an aqueous metal ion chelating composition containing an effective chelating amount of at least one multivalent metal ion chelating agent. Alternatively, in the foregoing contact step (b)(ii), an aqueous metal ion chelating composition preferably containing not more than about three weight percent chelating agent can be applied directly to the hair in the form of a rinse or spray.

The present invention beneficially minimizes the exposure of alkaline, chemically-relaxed hair to adsorption and retention of undesirable exogenous multivalent metal ion from the rinse water, chemical relaxer or both during the relaxer process. A particular benefit is that it ameliorates the adsorption and retention of undesirable deposits of exogenous alkaline earth metal ion present in no-lye chemical relaxers. Thus, in the practice of the method of this invention, the measurable total content of multivalent metal ion, and calcium and magnesium ion in particular, in the chemically-relaxed hair is less relative to hair chemically relaxed by conventional methods.

Still another benefit is that the method and delivery system of this invention allows the practitioner to use chemical relaxers, and no-lye type chemical relaxers in particular, in geographic regions where the local tap water supply is hard, or has a high content of multivalent metal ions, thereby avoiding the attendant problems associated with undesirable mineral buildup, and desirably enhancing the aesthetic attributes of the chemically relaxed hair. Additionally, the inventive method provides a resolution of the problem of deposition of alkaline earth metal ion on chemically-relaxed hair which can be carried out during the chemical relaxation process, thereby avoiding the need for separate multi step, mineral stripping chemical hair pre-treatments with potentially skin irritating heat and relatively high levels of metal ion chelating agent.

DESCRIPTION OF THE PREFERRED EMBODIMENTS

Figure 1:
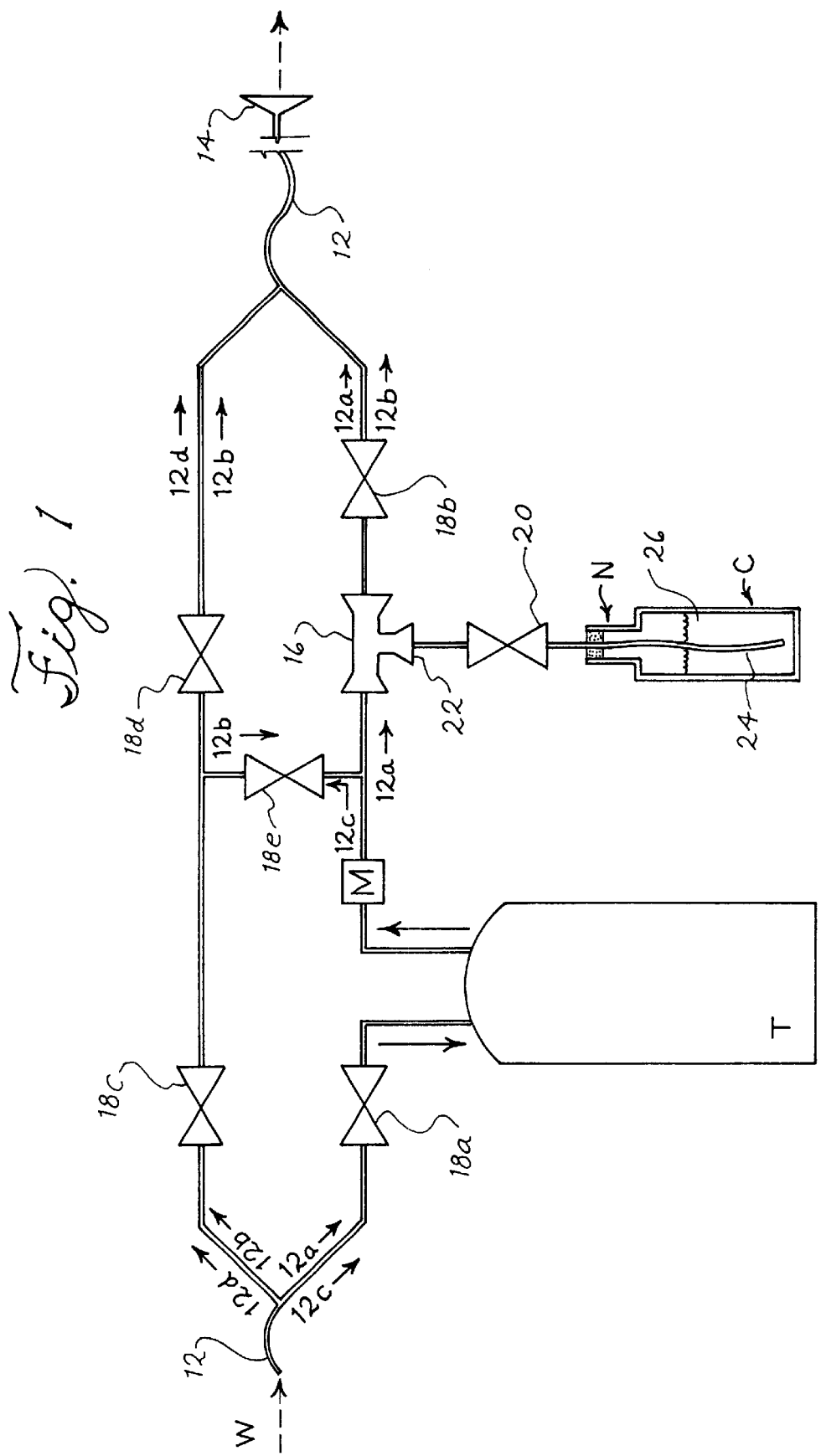
FIG. 1 illustrates schematically one preferred delivery system embodiment for delivery of an aqueous metal ion chelating composition concurrently with the rinse water during a hair relaxing process and in accordance with the present invention.

Naturally curly hair that has its natural curl chemically relaxed at a pH of above about 12, with a chemical hair relaxer in which the active hair-relaxing agent is a water-soluble strong chemical base, is generally referred to herein as "chemically-relaxed" hair. Commercially, such chemical hair relaxers employ strong bases that are physiologically tolerable, water-soluble, non-volatile relatively strong nitrogenous organic bases, and inorganic alkalis (caustic bases) that are capable of relaxing the natural curl in naturally curly hair. Examples of relatively strong nitrogenous organic bases conventionally employed include guanidine, hydrated guanidine (guanidinium hydroxide, guanidine hydroxide or the like), quaternary ammonium hydroxides, and the like. Examples of inorganic alkalis conventionally employed include inorganic alkali metal hydroxides, such as sodium hydroxide, potassium hydroxide or lithium hydroxide, and alkaline earth metal hydroxides, such as calcium hydroxide, or oxide thereof capable of forming hydroxide in water and the like.

The term "alkaline, chemically-relaxed hair" as used herein refers to naturally curly hair which has had its natural curl relaxed or straightened by contact with any one of the foregoing chemical relaxer compositions prior to having the residual alkalinity on the hair neutralized. The term "neutralized" as applied to chemically relaxed hair conventionally means that following the removal of chemical relaxer, as by rinsing with water, or an aqueous composition, the alkaline, chemically relaxed hair is contacted with a base neutralizing composition having a pH in the range of about 5 to about 7 and containing sufficient free acid to neutralize the residual alkalinity on the chemically relaxed hair. Such compositions are typically in the form of a shampoo and are conventionally known in the trade as a neutralizing or normalizing shampoo.

The term "undesirable multivalent metal ion" and "multivalent metal ion" in its singular and plural form is used interchangeably herein to refer to exogenous multivalent metal cation present in the relaxer, in the water used for rinsing the hair during the chemical relaxer process, or in both which can be adsorbed and retained by the chemically relaxed hair and can adversely affect the subjective aesthetic attributes of the hair (i.e., decrease luster, lessen conditioning results, decrease tactile feel and the like), damage the hair or interfere with the desired results of subsequent chemical treatments (i.e., hair dyes, permanent waves, relaxers and the like) or subsequent hair care treatments (i.e., shampooing, conditioning and the like). Undesirable multivalent metal ions that can be present in local hard tap water or well water include but are not limited to alkaline earth metal ions, such as calcium, magnesium, barium, strontium and the like; transition metal ions, such as copper, iron, manganese, nickel and the like; and heavy metal ions capable of forming heavy metal soaps with fatty acid, such as aluminum, lead, zinc and the like.

The term "hardness level" or "water hardness" as used herein refers to the commonly understood meaning of a water supply having dissolved calcium ($Ca^{+2}$) and magnesium ($Mg^{+2}$) minerals at a level expressed in terms of parts per million (ppm) or milligrams per liter (mg/l) concentration or grains per gallon (gpg). The term "soft water" as used herein refers to a water supply generally classified as having a level of hardness of not more than 17 ppm or mg/l (or expressed as gpg of less than 1).

It is recognized that water commonly is further generally classified as "slightly hard water" (level of hardness of 17–60 ppm or mg/l or 1–3.5 gpg); "moderately hard water" (level of hardness of 60–120 ppm or mg/l or 3.5–7.0 gpg); and "hard water" (more than about 120 ppm or mg/l or more than about 7 gpg). For convenience, the term "hard water" as used herein means water having a hardness level greater than 17 ppm and includes the foregoing general classifications, unless otherwise indicated.

The term "rinse water" as used herein refers to its commonly understood meaning as the water employed generally to rinse the hair at the various steps of a chemical hair relaxing process to remove the chemical hair relaxer from the hair and following related finishing steps, such as shampooing, conditioning and the like. For the practice of the method and system of this invention, soft rinse water is preferred having a hardness of not more than about one ppm, and more preferably of not more than about 0.1 ppm.

The term "metal ion chelating agent" and "chelating agent" is used interchangeably herein to refer to cosmetically acceptable compounds capable of forming water-soluble complexes with undesirable multivalent metal ions or prevent redeposition thereof on the hair. The term "metal ion chelating composition" or "chelating composition" is used interchangeably herein to refer to aqueous compositions having a physiologically tolerable pH containing an effective chelating amount of at least one multivalent metal ion chelating agent. Preferably, the pH of the metal ion chelating composition is in a range of about 6 to about 11, more preferably about 7 to about 8. The term "physiologically tolerable" as used herein means substantially non-irritating to human scalp and skin when contacted during a chemical relaxer process as disclosed herein.

Aqueous compositions useful for ameliorating or inhibiting the deposit of metal ion on alkaline, chemically-relaxed hair during the relaxation process preferably contain at least one alkaline earth metal ion chelating agent and more preferably at least two alkaline earth metal ion chelating agents.

Present preferred chelating agents useful herein, without being limited thereto, are selected from the group consisting of ethylenediaminetetraacetic acid (EDTA), diethylenetriaminepentaacetic acid (DTPA), hydroxyethylethylenediaminetriacetic acid (HEEDTA), nitrilotriacetic acid (NTA), ethanol diglycine (EDG), ethylenebis (hydroxyphenylglycine), N-dihydroxyethylglycine, iminodisuccinic acid (IDS), ethylenediaminedisuccinic acid (EDDS), polyaspartic acid, and water soluble alkali metal salts of each of the foregoing and the like employed singly or in combination. Preferably the alkali metal portion of the salts of the chelating agents are sodium or potassium. Particularly preferred are the disodium, trisodium and tetrasodium salts of EDTA and combinations thereof.

In practicing the method of this invention, (a) the curl in naturally curly human hair, whether of African or Caucasian origin, can be relaxed employing any commercially available hair relaxing composition having a pH above about 12 and containing an effective hair-relaxing amount of strong base applied to the hair according to the manufacturer's instructions. The chemical relaxer typically is applied to and distributed through the naturally curly portions of the hair and left in contact with the hair for a period sufficient to relax the natural curl to the extent desired. Those skilled in the hair relaxing arts recognize that such contact time with the hair can range from about 5 to about 30 minutes, more typically about 10 to about 20 minutes, depending on the resistance of the hair to chemical straightening and the result desired.

(b) Substantially immediately thereafter the chemical relaxer is then thoroughly and rapidly removed from the alkaline, chemically-relaxed hair and the adsorption and retention of multivalent metal ion ameliorated and inhibited as described below.

In a particularly preferred method aspect, the removal of the chemical relaxer from the hair and inhibition of undesirable multivalent metal ion adsorption and retention is effected concurrently. In this method aspect, aqueous metal ion chelating composition containing at least one multivalent metal ion chelating agent can be concurrently delivered with the rinse water to the alkaline, chemically-relaxed hair employing a delivery system adapted for use under a practical salon or home environment. A useful delivery system, is preferably modular, comprising in combination:

a) a conduit having at least one water inlet being operably and changeably connectable for liquid flow communication to a source of incoming raw water, at least one liquid outlet being preferably operably and changeably connectable to a liquid sprayer and at least one injector intermediate the water inlet and the liquid outlet, the injector further having an inlet being operably and changeably connectable for liquid flow communication with a source of aqueous metal ion chelating composition for concurrently receiving and admixing the received aqueous metal ion chelating composition with water flowing through the conduit;

b) a water softener tank intermediate the water inlet and the injector; and c) at least one valve located within the conduit, the valve being positionable and configured such that water flow through the conduit to the liquid outlet and liquid sprayer when associated therewith can be optionally channeled to:

i) pass through both the water softener and the injector for concurrently delivering an admixture of softened water having a hardness level of not more than 17 ppm, more preferably of not more than about 1 ppm, and a predetermined amount of the aqueous metal ion chelating composition; or ii) pass through the injector, bypassing the water softener, for concurrently delivering an admixture of predetermined amount of the aqueous metal ion chelating composition and raw incoming water.

Preferably the conduit of the modular delivery system includes a plurality of valves located therein, wherein each valve is positionable and configured such that water flow through the conduit directly to the liquid outlet and liquid sprayer when associated therewith can be further optionally channeled to:

iii) pass through the water softener for delivery of softened water having a hardness level of not more than 17 ppm, more preferably of not more than about 1 ppm; or iv) deliver raw incoming water.

A useful delivery system embodiment that can be employed under practical salon conditions for concurrently delivering an admixture of water and aqueous metal ion chelating composition is illustrated in FIG. 1.

FIG. 1 illustrates a modular delivery system, which in operative combination, comprises an apparatus 10 having a conduit 12 in which the water inlet of conduit 12 is shown operably and changeably connectable to a source of incoming raw rinse water W and the liquid outlet of conduit 12 is shown operably and changeably connectable to the liquid sprayer 14. The conduit 12 can be constructed of any commercial chemically inert piping capable of allowing water to flow therethrough. At least a portion of the piping is preferably flexible for easy connection to the water inlet and the liquid sprayer 14.

The type and dimensions of the piping are not limited so long as the water inlet of the piping can be adapted for attachment to a sink faucet or nozzle of a tap water source. A useful conduit 12 piping can be flexible, plastic tubing such as Tygon or Teflon tubing, having an internal diameter of about 0.5 inches (about 1.27 centimeters).

In FIG. 1, the injector 16 is positioned intermediate the water inlet and the liquid sprayer 14. The injector 16 further has an inlet 22 for receiving aqueous metal ion chelating composition 26 from container C for controllably and concurrently admixing a predetermined amount of the aqueous metal ion chelating composition 26 with rinse water flowing through the conduit 12 to the liquid sprayer 14. The chelating composition 26 is preferably packaged in a container or reservoir having an annular neck N configuration that can be changeably connected for liquid flow communication with the injector inlet 22, or which can be readily adapted for such connection.

The injector 16 embodiment illustrated in FIG. 1 is connectable to a control valve 20 positioned intermediate the injector 16 and the neck N of container C of aqueous chelating composition 26. Control valve 20 can be any one-way valve (such as a stopcock or the like) capable of controlling the flow of preselected amounts of aqueous chelating composition 26 to be received by the injector 16 for admixture and delivery concurrently with the rinse water as long as the valve material is chemically non-reactive with the chelating composition.

In the apparatus embodiment illustrated in FIG. 1, liquid flow communication of the injector to the container C of aqueous chelating composition 26 is achieved with a flexible suction tube 24 changeably connectable to the control valve 20 and insertable to a sufficient depth in container C to so that liquid metal ion chelating composition 26 can flow therethrough and be received by injector 16. The suction tube 24 can be of any flexible tubing, such as Tygon or the like, so long as it is chemically unreactive with the metal ion chelating composition. A useful suction tube can have an internal diameter of about 0.375 inches (about 0.95 centimeters). Injector 16 can thus admix the received liquid metal ion chelating composition with oncoming rinse water flowing through conduit 12 for delivery to the liquid sprayer 14. The injector in FIG. 1, illustrates a venturi-type injection system operating on hydraulic flow and pressure to draw the predetermined amount of liquid metal ion chelating composition 26 from container C.

A useful water pressure of rinse water passing through the conduit to the adapter is in the range of about 12–13 pounds per square inch (psi). For quickly removing the chemical hair relaxer, a water pressure of at least 12 psi or greater is preferred. In locations experiencing low water pressure, a booster pump for increasing the pressure of the water flowing to or through the conduit of the delivery system can be employed.

Alternatively, liquid flow communication can be achieved with the container C of aqueous metal ion chelating composition positioned in operative gravity feed connection with control valve 20 and injector 16 to deliver the composition 26 to injector 16 for gravity admixing. In this case, the suction tube can be omitted and the control valve 20 can be adjusted to control the amount and rate of admixing of aqueous metal ion composition received.

It is recognized that the container C can be any suitable reservoir for the aqueous metal ion chelating composition that can be readily adapted for use with the delivery system. Thus, the container C can be a refillable reservoir or a single use package.

The apparatus embodiment in FIG. 1 illustrates a modular delivery system in which the control valve 20 is a separate element changeably connectable to the injector inlet 22 intermediate the injector 16 and the container C, but is not intended to be so limited. It is recognized that the injector 16 can be configured to contain a one-way valve, thereby eliminating the necessity of a separate control valve element, and the neck N of container C can be changeably connected for liquid flow communication directly to the injector inlet 22.

In another delivery system aspect, following the delivery of metal ion chelating composition to the alkaline chemically relaxed hair, the container C can be removed and substituted by a container of post-relaxer liquid hair conditioning composition, such as a creme rinse and the like, for delivery in like manner by way of the injector 16. Alternatively, the conduit can be modified to include a second injector and appropriate control valves along the path for delivery of liquid post-relaxer hair conditioning compositions to the liquid outlet.

In FIG. 1, a water softener unit T is positioned intermediate the water inlet of conduit 12 and the injector 16. Preferably the water is softened to a hardness level of not more than 17 ppm, more preferably of not more than about 1 ppm, most preferably of not more than about 0.1 ppm calcium. A meter M is preferably positioned intermediate the water softener T and the injector 16. Any commercially available one-way water meter can be employed. The water softener T can be any commercially available water softening system, such as a tank or deionizer unit, preferably comprising an ion-exchange resin with sodium ion as the exchangeable cation. If a booster pump is employed, it is preferably positioned intermediate the water softener unit T and the meter M. For ready replacement of the water softener unit T, and the booster pump, when present, flexible piping is preferred.

In the delivery system embodiment illustrated in FIG. 1, the apparatus 10 of the delivery system is configured to include a plurality of valves, 18a, 18b, 18c, 18d, and 18e, located within the conduit 12. Each valve is positioned and configured such that the water flow through the conduit 12 to the sprayer 14 can be optionally channeled through a selected defined path. In FIG. 1, the apparatus 10 defines four optional paths, 12a, 12b, 12c, 12d, along conduit 12 for channeling rinse water W flowing to the liquid sprayer 14. For controlling the water flow, valves 18a, 18b, 18c, and 18d can be any type of one-way valve and valve 18e can be any type of bi-directional valve, that can be positioned to operatively define the liquid flow selected paths along conduit 12. The ability to optionally channel the path of the water flow provides the user versatility in employing the apparatus 10 of the inventive delivery system, particularly under practical salon usage conditions.

Thus, in selected path aspect 12a along conduit 12 as illustrated in FIG. 1, an admixture of soft rinse water and chelating composition is concurrently delivered to the liquid sprayer 14. In this delivery aspect, valves 18a and 18b are open to define path 12a along conduit 12, valves 18c, 18d, and 18e are closed to water flow, a container C of aqueous chelating composition 26 is changeably connected in liquid communication to the control valve 20 and the control valve 20 is changeably connected to the injector inlet 22 of the injector 16. The control valve 20 can be opened for liquid flow so that the injector 16 can receive a controlled preselected amount of aqueous chelating composition 26 from container C and the metered oncoming rinse water W flowing from the water softener T at its ambient pressure aspirates and admixes with the injected chelating composition 26. A useful ambient pressure for rinse water passing through the injector is at least 12 psi, preferably at least about 13 psi.

In selected path aspect 12b along conduit 12 illustrated in FIG. 1, an admixture of predetermined amount of the aqueous chelating composition 26 and raw incoming rinse water can be concurrently delivered to the liquid sprayer 14 by opening valves 18c, 18e, and 18b to define path 12b, and closing valves 18a and 18d, to bypass the water softener tank T. This configuration allows raw incoming rinse water at ambient pressure of about 35–40 psi to flow through to the injector 16 and admix with aspirated aqueous chelating composition 26 when the injector 16 is operably connected to receive chelating composition 26 (as previously described for path 12a). When path 12b is chosen, if care needs to be taken to avoid a backflow of raw water into the Meter M through to the water softener T, an additional one-way valve can be located intermediate the Meter M and the injector 16.

In selected path aspect 12c along conduit 12 illustrated in FIG. 1, soft water is delivered directly to the liquid sprayer 14 by opening valves 18a, 18e, and 18d to define path 12c, and closing valves 18c, 18b, and control valve 20 to liquid flow. Alternatively, soft water can also be delivered by path 12a, described above, so long as control valve 20 is closed.

In selected path aspect 12d along conduit 12 illustrated in FIG. 1, raw water can be delivered directly to the liquid sprayer 14 by opening valves 18c and 18d to define path 12d and closing valves 18a, 18b, and 18e to liquid flow.

The apparatus of the delivery system is preferably modular so that it can be packaged for sale, storage, portability and the like and be readily assembled for use or disassembled by the user.

Preferably, before injection, the source of liquid aqueous metal ion chelating composition contains a total amount of metal ion chelating agent calculated on a total composition basis of not more than about five weight percent, preferably not more than about four weight percent, most preferably not more than about three weight percent. Upon injection, the metal ion chelating composition can be diluted with rinse water, on a parts by weight basis from about 1:1 to about 1:10, more preferably from about 1:4 to about 1:8 in the admixture delivered by the liquid sprayer 14.

A particularly preferred source of liquid metal ion chelating composition for use in the delivery system of this invention comprises, prior to injection, on a total composition basis, about 1 weight percent to not more than about 3 weight percent of at least one alkaline earth metal chelating agent and which on injection preferably is diluted with the rinse water to a concentration of from about 0.1 to not more than about 1 weight percent in the resulting admixture delivered to the hair.

Particularly preferred is a pre-injection composition comprising on a total composition basis: about 1 weight percent to about 1.5 weight percent of ethylenediaminetetraacetic acid disodium salt; about 1 to about 1.5 weight percent of ethylenediaminetetraacetic acid tetrasodium salt; and the remainder being water and optionally, cosmetic adjuvants.

The pre-injection composition is preferably diluted, on a parts by weight basis from 1:1 to about 1:10, preferably to about 1:8, with rinse water to deliver a dilute admixture, preferably in the form of a spray rinse comprising on a total admixture basis: about 0.1 to about 0.25 weight percent ethylenediaminetetraacetic acid disodium salt; and about 0.1 to about 0.25 weight percent ethylenediaminetetraacetic acid tetrasodium salt.

Surprisingly, an admixture of water containing, on a total admixture basis, about 0.1 to not more than 1 weight percent, more preferably not more than about 0.5 weight percent, most preferably not more than about 0.3 weight percent total alkaline earth metal chelating agent ameliorated or inhibited the deposition of multivalent metal ion, particularly calcium ion on alkaline chemically-relaxed hair. Further, it was found that by employing for the admixture rinse water having a hardness of not more than about 0.1 ppm, the retention of alkaline earth metal ion deposit on the chemically-relaxed hair was inhibited such that the total alkaline earth metal content of the chemically-relaxed hair was either substantially unchanged relative to that present before chemical relaxation or, if higher, the retention was ameliorated by at least about 40 weight percent, more preferably by at least about 80 weight percent relative to chemically-relaxed hair not contacted with such admixture. It was found that such amelioration and inhibition was achieved in a contact period ranging from at least about 2 minutes to not more than about five minutes.

Where it is not possible or convenient to employ the apparatus of the inventive delivery system, the inventive method can be practiced in one alternate method aspect, whereby the removal of the chemical relaxer from the hair can be effected by (i) rinsing with water having a hardness level of not more than 17 ppm, preferably soft water, deionized water, or distilled water, preferably having a temperature in the range of about 30° C. to about 37° C. and then (ii) substantially immediately thereafter contacting the water-rinsed, alkaline, chemically-relaxed hair with an aqueous composition containing at least one multivalent metal ion chelating agent for a period sufficient to remove substantially all, or a portion of at least one selected exogenous multivalent metal ion, particularly calcium and magnesium, adsorbed and retained by the alkaline, chemically-relaxed hair from the chemical relaxer, the rinse water or both. A contact period of not more than about 5 minutes was found sufficient to provide chemically relaxed hair having a lower total content of the at least one selected exogenous multivalent metal ion relative to the amount of that multivalent metal ion found in the hair in the absence of such contact.

Preferably soft water having a hardness level of not more than 1 ppm is employed in step (i). The adsorption and retention of exogenous multivalent metal ion is exacerbated if tap water is employed in step (i), but can be ameliorated by practicing step (ii).

The metal ion chelating composition can be manually applied in step (ii), preferably as a liquid pour-over rinse or pump spray, directly to the water-rinsed alkaline, chemically relaxed hair. The rinse or spray can be applied at least once, followed by a towel blot or water rinse, and can be reapplied with intervening towel blotting or water rinses as desired.

When the metal ion chelating composition is applied manually to alkaline chemically-relaxed hair in the form of a liquid aqueous pour-over rinse or as a spray delivered from a manual pump spray, the concentration of total metal ion chelating agent present, calculated on a total composition basis, preferably is in the range of about 0.5 weight percent to not more than about 3 weight percent, more preferably not more than about 2 weight percent, most preferably not more than about 1 weight percent with the remainder water and optional cosmetic adjuvants.

The metal ion chelating composition can also be manually applied to the alkaline, chemically-relaxed hair in the form of an aqueous gel, emulsion or the like. The aqueous emulsion can be in the form of a pourable lotion or non-runny, viscous cream.

In another preferred method aspect, where it is not possible or convenient to employ the apparatus of the inventive delivery system, the aqueous metal ion chelating composition can be manually applied in step (ii) by carrying the composition on a sheet material substrate as a wipe embodiment. Wipe embodiments can be in the form of wet wipes or dry wipes. "Wet wipes" can also be referred to as "pre-moistened wipes" or "towelettes", because they include a substrate that is moistened, as by wetting and impregnating the substrate with a liquid composition, prior to use by the user. Preferably wet wipes comprise a substrate which is moistened prior to packaging, such as in a generally moisture impervious container or wrapper. Alternatively, following impregnation, the impregnated wipe can be allowed to substantially dry, be packaged as a substantially dry wipe for storage and then re-moistened, as by spraying with soft water (deionized or distilled), immediately before use.

Wipe embodiments can be prepared by impregnating a porous, flexible, sheet material with an aqueous composition containing at least one metal ion chelating agent. The sheet material can be any flexible chemically inert substrate that can absorb sufficient aqueous chelating solution to form a wet wipe capable of deforming sufficiently to contact alkaline, chemically-relaxed hair and releasing an effective chelating amount of chelating composition to the hair.

Suitable wipe sheet substrates can comprise woven or non-woven web formed of natural fibers, synthetic fibers or combinations thereof. Preferred are paper sheets comprised of cellulosic fibers of natural or synthetic origin, or cloth of natural fibers, such as wood pulp, cotton, linen, or rayon or blends of natural and synthetic fibers, such as polyester and polypropylene. One presently preferred sheet material is paper crepe of 23 pound weight basis.

Various methods of forming suitable nonwoven and woven fibrous web substrates are known in the paper making arts and textile arts. For example, nonwoven dry forming techniques include air-laying, or wet laying, such as on a papermaking machine or can be melt blown, spun bonded and the like. Those skilled in the art will recognize that the kind of sheet material is limited only by its ability to sorb and retain sufficient chelating composition to release chelating composition on contact with the alkaline, chemically-relaxed hair.

Those skilled in the art will also recognize that the size of the wet wipe sheet is not limited and can be readily determined for convenience by the manner in which the wipe will be employed. Thus, the size of the wet wipe can vary as desired to either hold individual tress lengths of hair or to cover the entire head of hair. When the wipe is sized to hold and contact the alkaline chemically-relaxed hair on an individual tress by tress basis, an individual tress can be enveloped by the wet wipe and wiped by hand directionally away from the scalp along the full length of the tress for about one minute or until the tress feels or is visually improved. Alternately, the foregoing wet wipe can be used in a towel-like rubbing fashion over the head hair. A useful wipe size without being limited thereto, can be a rectangle of about 20 cm (about 7.9 in) by about 30 cm (about 11.8 in) or about 15 cm (about 5.9 in) by about 20 cm (about 7.9 in). It was found that effective chelation could be achieved on a head of hair with a contact time of about 2 to about 4 minutes. A useful amount of chelating composition present on such a wet wipe can be in range of about 0.05 to about 0.2 grams.

For impregnation, a useful wipe sheet can be saturated with a previously prepared metal ion chelating composition employing a sheet:bath weight ratio of from about 1:2 to about 1:3 employing conventional impregnating techniques such as adsorption or immersion. Preferably, the metal ion chelating composition contains a concentration of total alkaline earth metal chelating agent in the range of about 1 weight percent to about 4.5 weight percent, more preferably of about 2 to about 4 weight percent, calculated on the total weight of the chelating composition employed for impregnating the wipe sheet material.

In one impregnating method aspect, the wipe substrate can be packaged and saturated in situ. For example, the wipe substrate can be folded and inserted into a preformed liquid impermeable package, such as a pouch, having one opening and then adding the impregnating liquid aqueous metal ion chelating composition to allow the liquid to saturate and be absorbed by the wipe substrate in situ. The package or pouch can then be sealed for storage. In another impregnating method, the wipe can be immersed in the impregnating liquid and then used immediately or packaged in a moisture impermeable container as a wet wipe for storage.

For storage, the wet wipe embodiment can be packaged in a moisture impermeable container, either as individual packaged wipes such as in heat sealed packets or the like, or as stacked wipes in covered dispensers to prevent evaporation of the aqueous chelating composition.

Metal ion chelating compositions can also contain conditioning agents for the hair, pH adjusting acid or base, viscosity modifiers, preservatives, fragrances and like optional cosmetically acceptable adjuvants employed in the hair relaxing and styling arts, so long as the ingredient employed does not react with the chelating agent or interfere with its metal ion chelation capability. The term "conditioning agents" as used herein collectively includes hair conditioners, emollients, lubricants and the like, obtained from natural and synthetic sources conventionally used by the cosmetic industry hair care products to enhance the subjective attributes of hair, prior to or after chemical treatments and during routine hair care maintenance.

Those skilled in the cosmetic arts are familiar with conventional cosmetic adjuvant ingredients which are commercially available from a number of sources. Descriptions of and suppliers of conventional ingredients can readily be found in a number of trade publications. For convenience, ingredients generally will be referred to by the industry recognized standardized designations given them in the *International Cosmetic Ingredient Dictionary*, Sixth Edition, published by The Cosmetic, Toiletry, and Fragrance Association, Washington, D.C. (1995) commonly referred to as "INCI" names.

Alkaline, chemically-relaxed hair that has been treated with a metal ion chelating composition in accordance with this invention can be further washed or rinsed with a base neutralizing composition, such as a shampoo, conditioner rinse or the like, having a pH of about 5 to about 7, as is conventionally practiced in the hair relaxing arts.

It was found that naturally curly hair readily adsorbs and retains exogenous alkaline earth metal ion on exposure to tap water containing calcium and magnesium ions during routine washing with shampoo. Alkaline, chemically-relaxed hair was found particularly receptive to adsorption and retention of alkaline earth metal ion, particularly calcium and magnesium, during the chemical relaxation process. Surprisingly, the calcium content of the alkaline, chemically-relaxed hair increased regardless of whether the strong base employed in the chemical relaxer was an organic base (i.e., no-lye type relaxer) or an alkali metal hydroxide. While the mechanism for this deposition is not fully understood, and without being bound by any theory, it is believed that chemical relaxation at a pH above about 12 increases receptive anionic sites or anionic moieties or both in the alkaline chemically-relaxed hair. It is also believed that adsorption and retention of alkaline earth metal cations is probably maximized while the chemically-relaxed hair is still alkaline, i.e., substantially immediately following removal of the strong base relaxer before neutralizing the residual alkalinity on the hair.

The alkaline earth metal ions, calcium (Ca) and magnesium (Mg) are particularly common undesirable ions present in tap water. Intact naturally curly hair as received from a commercial supply house typically contained not more than about 3,500 ppm (mg/kg) total Ca and not more than about 450 ppm (mg/kg) total Mg. It was found that the total calcium and magnesium content of the commercial hair respectively could readily increase by more than 1.3 fold and more than 1.4 fold by simply washing the hair with slightly hard tap water having an average hardness of about 39 ppm Ca and about 11 ppm Mg, whereas rinsing with deionized water produced substantially no increase.

During the subsequent chemical relaxation of naturally curly hair, it was surprisingly found that the total calcium content in the hair could further increase at least 2.9 fold and the total magnesium content could increase more than 4 fold regardless of whether the chemical relaxer was a organic base (no-lye type) or inorganic base (lye-type), when slightly hard rinse water was employed. When deionized water was employed for rinsing during the chemical relaxation process, no increase in the content of the either mineral occurred. Thus, the problem of alkaline earth mineral deposit remaining on hair chemically relaxed by conventional methods was found to be exacerbated as the hardness of the rinse water employed increases.

It was also found that the sorption of other multivalent metal ions by alkaline chemically-relaxed hair was exacerbated when using slightly hard rinse water during the chemical relaxer process, compared to that present when soft water rinsing was employed, regardless of whether no-lye type or lye-type relaxer was used. It was found that in hair chemically relaxed with no-lye type relaxer, the total content of an exogenous alkaline earth metal ion, selected from Ba, Ca, Mg and Sr increased at least 2 fold, and of either an exogenous transition metal ion, selected from Cu, Fe, Mn, and Ni, or of an exogenous heavy metal ion selected from Al, Pb and Zn increased at least 1.1 fold when slightly hard tap water was used relative to the total content found of each selected metal ion when soft water was used.

The aesthetic attributes of the hair which a person can discern include the visible appearance of the hair such as sheen, dullness, color and the like, and its tactile or handling characteristics, such as combing ease, manageability, stylability, softness, smoothness, moisture, dryness, mobility and the like. These hair attributes are important to a consumer and the acceptance or rejection of a product for the hair depends on its ability to maintain or enhance desirable hair attributes, or improve undesirable hair attributes or both. In particular, residue on the hair can interfere with the intended cosmetic effectiveness of a product for the hair, which in turn negatively affects the aesthetic attributes of the hair.

Some persons, for health reasons or the like, have hair attributes which are somewhat undesirable. For example, the hair may tend to be naturally dry or lackluster or limp. For these persons, any undesirable deposition on the hair is particularly problematic. Thus, avoiding further adsorption and retention on the hair of insoluble alkaline earth metal constituents deposited from chemical relaxation is important.

It was judged that when an increase in total alkaline earth mineral content adsorbed by the hair exceeds at least about 30% calcium and about 40% magnesium, a decrease in one or more desirable hair attributes can be expected to occur.

The following Examples illustrate the invention further with generally preferred embodiments, ingredients and methods, but are not intended to be limiting.

EXAMPLE 1

Materials and Methods

Preparation of hair tresses. Hair tresses, each about 4 to about 5 centimeters (cm) in length, and weighing about 1 gram (g) were prepared from African-American hair of natural brown to black color obtained from De Meo Brothers (New York). The hair was classified as "excessively curly", i.e., had a tight, kinky curl. The root (scalp) portion of each tress was secured to a canvas cloth tab with water insoluble glue. Each secured tress was then cleaned by washing it for about one to about two minutes with about 1 g of shampoo composition (A), rinsed with tap water, combed until the fibers were detangled and allowed to air dry at ambient room temperature and humidity.

| Shampoo Composition A | |
|---|---|
| Ingredient | Active Weight % |
| Ammonium lauryl sulfate | 10 |
| Lauramide DEA | 3 |
| Citric acid | 0.5 |
| EDTA, disodium | 0.2 |
| Preservatives | q.s. |
| Fragrance | q.s. |
| Water, deionized to 100% | q.s. |
| pH 5–5.5 | |

Unless otherwise indicated, naturally curly hair tresses were prepared and cleaned as described prior to subsequent treatments.

Preparation of Hair Leachate for Elemental Analysis

For analysis of alkaline earth metal ion content in the hair, 0.2 g of the substantially dry hair from each tress was carefully weighed into a Philips beaker of 250 milliliter (ml) volume and a leachate of digested hair was prepared. For digestion, dilute acid (50 g each of aqueous hydrochloric acid (25% w/w) and aqueous nitric acid (1% w/w)) was added to each beaker containing hair. The beaker was then covered with a watch glass and the contents stirred mechanically overnight employing a GYROTORYO® platform shaker Model G2 (New Brunswick Scientific Company, Inc., Edison, N.J.) set at slow speed (about 100 revolutions per minute). The resulting leachate was then transferred into a 100 ml volumetric flask and deionized water added to volume. The leachate had a pH of less than 2.

The total alkaline earth metal ion (calcium or magnesium) content of the hair leachate was analyzed by standard analytical flame Atomic Absorption Spectroscopy (AAS) and Inductively-Coupled Plasma (ICP) techniques. The concentration in milligrams/kilogram (mg/kg) of alkaline earth metal ion in the test hair leachate sample was determined from a calibration curve plotted for a range of different standard solutions of the alkaline earth metal ion.

All alkaline earth metal ion chelating agents employed were analytical grade reagents purchased from commercial chemical supply houses.

Source of Tap Water and Soft Water

Unless otherwise indicated, the tap water employed was Lake Michigan water processed from the city of Chicago, Ill. According to chemical analysis reports of the Department of Water of the city of Chicago, the tap water has an average hardness of about 39 ppm calcium (Ca) and about 11 ppm magnesium (Mg) in distributed water in central, south, and north water districts. The analysis of the Lake Michigan tap water obtained in the testing laboratory had a hardness of about 37 ppm Ca and about 11 ppm Mg. This tap water is generally classified as slightly hard water. The soft water was obtained by passing the tap water through a water softening tank containing ion-exchange resin with sodium as the exchange cation as described in Example 3 below.

A quantitative analysis by ICP technique also was made of eleven multivalent metal ions selected from the classes of alkaline earth metals (Ba, Ca, Mg, Sr), transition metals (Cu, Fe, Mn, Ni) and heavy metals (Al, Pb, Zn) present in tap water (Lake Michigan) and in soft water. The metal ion concentration determined as mg/l (ppm) is shown in the following charts.

| | Total Metal Concentration (mg/l) | | | |
|---|---|---|---|---|
| | Alkaline Earth Metal | | | |
| Water | Ba | Ca | Mg | Sr |
| Tap Water (Lake Michigan) | 0.02 | 33.43 | 9.213 | 0.11 |
| Soft Water | N.D. | 0.021 | 0.005 | N.D. |
| Detection Limits (DL) in ppb | | | | |
| | 0.5 | 0.5 | 0.5 | 0.5 |

N.D.: Not detected or below DL

| | Total Metal Concentration (mg/l) | | | | | | |
|---|---|---|---|---|---|---|---|
| | Transition Metal | | | | Heavy Metal | | |
| Water | Cu | Fe | Mn | Ni | Al | Pb | Zn |
| Tap Water (Lake Michigan) | 0.025 | N.D. | N.D. | 0.046 | 0.186 | 0.026 | N.D. |
| Soft Water | 0.005 | N.D. | N.D. | 0.033 | 0.083 | 0.012 | N.D. |
| Detection Limits (DL) in ppb | | | | | | | |
| | 2 | 2 | 1 | 5 | 4 | 30 | 2 |

N.D.: Not detected or below DL

EXAMPLE 2

This example illustrates the total Ca and Mg content, based on elemental analysis of commercial naturally curly hair from two different hair lots (Lot 1 and Lot 2) as supplied (Tresses A), and its retention of Ca and Mg after being exposed to slightly hard tap water (about 37 ppm Ca) during washing (Tresses B) with Shampoo A as described in Example 1, and following subsequent chemical relaxation with a commercial no-lye type chemical relaxer for resistant hair having a pH of greater than 13, AFFIRM® Sensitive Scalp (SS) relaxer (Avlon Industries, Inc.) (Tresses C). For comparison, the retention of Ca and Mg by deionized water rinsed chemically relaxed hair was also included (Tress D).

The results are shown in Table 1.

TABLE 1

| | | (mg/kg) | |
|---|---|---|---|
| Tress/Lot | Chemical Treatment | Ca | Mg |
| A 1 | None, as supplied | 2,600 | 305 |
| B 1 | None, washed (note 1) | 3,400 | 440 |
| C 1 | Washed, chemically relaxed, tap water rinsed (notes 1, 2) | 10,200 | 1,880 |
| D 1 | Washed, chemically relaxed, deionized water rinsed (notes 1, 2) | 4,450 | 330 |
| A 2 | None, as supplied | 1,990 | na |
| B 2 | None, washed (note 1) | 2,660 | na |
| C 2 | Washed, chemically relaxed tap water rinsed (notes 1, 2) | 7,831 | na |

Note 1: Washing procedure of Ex. 1 with Shampoo A.
Note 2: The SS relaxer product has two-parts, a relaxer creme and activator liquid, that are mixed together for use. About seven grams relaxer creme containing about 5.5% calcium hydroxide and about two grams activator liquid containing about 27.2% guanidine carbonate were mixed together and about three grams of the admixture was applied to a one gram hair tress. The chemical relaxer was left in contact with the hair for about 18 minutes and then removed by rinsing with tap water for about two to about three minutes.

The elemental data show that when slightly hard tap water was employed, the total Ca content of the hair as supplied (Tresses A) on average increased more than about 1.3 fold from shampooing (Tresses B) and on average further increased about three fold from subsequent chemical relaxation (Tresses C). The elemental data also show that the total Mg content of the hair as supplied (Tresses A) increased about 1.4 fold during shampooing in slightly hard water (Tress B) and further increased by more than four fold during the chemical relaxation step when slightly hard tap water was employed (Tress C). The tap water rinsed chemically-relaxed hair was also judged visually dull in appearance and had a heavy tactile feel.

The data obtained when deionized water was employed (Tress D) demonstrates the benefit of minimizing exposure to rinse water having calcium and magnesium metal ions present during the chemical relaxation of hair, because relative to shampooed hair (Tress B), the total Ca content increased not more than 1.3 fold and the total Mg content did not increase, remaining substantially the same as the hair as supplied (Tress A).

For comparison, an attempt was made to remove calcium deposit from a tress from lot 2 prepared according to the procedure of Example B, Table 1, by employing a commercial product sold for professional salon use as a "pre-chemical service treatment" for removing "problem" metals, such as removing copper, from copper contaminated hair.

The product was L'AVANTGARDE Clean Canvas hair Primer and Purifier (L'Avant Garde, Inc., Simi Valley, Calif.), a liquid having a measurable pH of 7.7 and was applied to the hair tress following the directions of the manufacturer. The directions call for three steps, i.e., to (1) apply the product to dry hair with a brush, (2) cover the hair with a plastic cap and place under heat for 5 minutes (or 10 to 15 minutes for extreme buildup), and (3) add water, lather and rinse. According to the manufacturer, the process and product is reportedly described in U.S. Pat. No. 5,635,167 to Said et al., the relevant disclosures of which are incorporated herein by reference, and the product reportedly is an aqueous surfactant solution containing a blend of metal ion chelating agents at a concentration of between 4% to 25%.

After the commercial product was applied to the hair tress, the tress was covered with a plastic wrap and heated at a temperature of about 55° C. for at least 5 minutes and then rinsed with the slightly hard tap water.

The elemental analysis results showed that the attempt was unsuccessful, because the total Ca content after the commercial treatment was 3,305 mg/kg, representing more than a 1.6 fold increase with respect to the initial calcium content of the hair as supplied and more than a 1.2 fold increase relative to the shampooed hair (Tress B).

EXAMPLE 3

This example illustrates the effective use under simulated practical salon conditions of an inventive delivery system embodiment generally as shown in FIG. 1 employing Chelating Composition (A) having the formula shown in Table 2 prior to injection for admixture with soft rinse water passing through path 12a along conduit 12 to the sprayer 14.

TABLE 2

| CHELATING COMPOSITION A | |
|---|---|
| Ingredient | Active Weight % |
| EDTA, tetrasodium | 1.04 |
| EDTA, disodium | 0.96 |
| Preservative | q.s. |
| Deionized water to 100% | q.s. |
| pH 7.4 | |

For injection and admixture of chelating composition (A) with rinse water flowing along path 12a or 12b illustrated in FIG. 1, approximately 1,000 grams of the chelating composition (A) was contained in a bottle of a liter (32 fluid ounce) holding capacity and placed for liquid flow communication with the one-way control valve 20 and the injector 16. The control value 20 was a venturi type injection system operating on hydraulic flow and pressure. Tap water having a hardness of about 37 ppm Ca was softened to a hardness level of about 0.064 ppm by passing it along path 12a to the water softener tank T.

The water softening tank system employed included about one-quarter cubic feet of a commercially available ion-exchange resin with sodium ion as the exchange cation. The resin was enclosed in a cylinder of about 6 inches×8 inches (about 15.24×20.32 cm.) and was capable of tolerating a temperature of up to about 49° C. (about 120° F.). The water softening system had a maximum water-softening capacity of 7200 grains (as $CaCO_3$). The incoming flow rate of the water to the water softener system was about 40–50 psi (about 2–4 gallons/minute) and the flow rate of softened water or admixture of soft water and metal ion chelating composition to the injector 16 was about 12–14 psi (about 0.6 to 0.7 gallons/minute).

The soft water was then metered to the injector 16, where the soft rinse water at an ambient pressure of about 13 psi aspirated the chelating composition (A), diluting one part by weight of the chelating composition with eight parts by weight soft water to deliver the resulting admixture (SA) to the sprayer 14. Thus the dilute chelating rinse (SA) spray contained a total of about 0.22% chelating agent (about 0.115% EDTA, tetrasodium salt and about 0.107% EDTA, disodium salt). The temperature of the rinse water spray was set for about 35–45° C. (about 95–115° F.).

Six tresses (one gram each) were prepared as described in Example 1, Table 1, for tress A from Lot 2, having an initial total Ca content of about 1,990 mg/kg.

One set of three tresses (Group I) was chemically relaxed for about 18 minutes employing the commercial no-lye type chemical relaxer, AFFIRM® Sensitive Scalp (SS) relaxer for resistant hair (Avlon Industries, Inc., Bedford Park, Ill.). The relaxer was prepared for use and applied as described in Example 2, Table 1, Note 2, except that the chemical relaxer was removed from each tress separately by: (A) rinsing one tress with slightly hard tap water delivered along path 12d (illustrated in FIG. 1); (B) rinsing a second tress with soft water (0.064 ppm Ca) delivered along path 12c (illustrated in FIG. 1); and (C) rinsing a third tress with the admixture of soft water (0.064 ppm Ca.) plus chelating composition (AA) delivered along path 12a (illustrated in FIG. 1). Each tress was so rinsed for about two minutes, air dried, and then analyzed for total Ca as described in Example 1.

A second group of three tresses (Group II) was chemically relaxed for about 18 minutes employing the commercial chemical relaxer, AFFIRM® resistant strength (Avlon Industries, Inc.) containing about 2.2% sodium hydroxide and having a pH greater than about 13, applying about three grams relaxer to each one gram tress. The chemical relaxer was then removed following the same rinsing procedure for tress A, B and C as in Group I.

The results are shown in Table 3 along the calculated % inhibition in retained Ca relative to that retained by the tap water rinsed tress control (A) as indicated in each Group of tresses.

TABLE 3

| Study Group | Tress | Rinse | Ca (mg/kg) | % Inhibition |
|---|---|---|---|---|
| I | A | Tap water | 7,418 | |
| I | B | Soft water | 3,220 | 57 |
| I | C | Chelating (SA) | 1,982 | 73 |
| II | A | Tap water | 8,720 | |
| II | B | Soft water | 2,520 | 71 |
| II | C | Chelating (SA) | 1,800 | 79 |

Surprisingly, the dilute chelating rinse SA, containing about 0.22% chelating agent, inhibited the sorption and retention of calcium ion by more than 70% compared to Ca sorbed and retained from tap water on the alkaline, chemically-relaxed hair regardless of relaxer used. This beneficial amelioration in the sorption of Ca by alkaline, chemically-relaxed hair was greater than that achieved by simply using a soft water rinse in both cases. In effect, the total Ca content of the hair was not increased during the chemical relaxation when the delivery system and dilute chelating admixture rinse (SA) was employed.

In further tress studies similar to Group I, increasing the rinse time from about two minutes to about three minutes increased the % inhibition of calcium by soft water alone (I-B type) or in combination with the chelating composition (I-C type) by about another 15% and 13%, respectively. In further tress studies similar to Group II, increasing the rinse time of from about two minutes to about three minutes produced a relatively small increase in % inhibition of calcium by soft water alone (II-B type) or in combination with the chelating composition (II-C type) of about 2% and 3% respectively.

The surface of the tresses from study Groups I and II were observed under Scanning Electron Microscope (SEM) technique employing a Lica-Zeise Leo 435 VP scanning electron microscope at a level of 1800 to 2200 times magnification. In the SEM micrographs of the Group I study, the tap water rinsed (A) tress had observable particle deposits on the surface which obscured the cuticle boundaries, whereas the surface of both the soft water rinsed (B) and chelated rinsed (C) tresses had a very clean appearance and cuticle boundaries were distinct. In the SEM micrographs of the Group II study, the surface of the tap water rinsed (A) tress appeared coated and the cuticle boundaries were unclear whereas the surfaces of both the soft water rinsed (B) and chelated rinsed (C) tresses had a very clean appearance and cuticle boundaries were distinct.

The desirable attributes of the hair rinsed with soft water, i.e., lighter feel, softness, smoothness, more moisture and mobility, sheen and manageability, relative to that of hair rinsed with tap water, was judged to be further enhanced on the tresses rinsed with the admixture of metal ion chelating composition and soft water.

EXAMPLE 4

In this comparative example, the chemical relaxation and rinsing procedure of Example 3 for the Group II study was repeated for tresses (A), (B), and (C). A fourth tress (D), was similarly chemically relaxed and rinsed following the procedure of Group II Tress C, except that the rinse admixture was prepared from chelating composition (B) having the formula shown in Table 4 prior to injection.

TABLE 4

CHELATING COMPOSITION B

| Ingredient | Active Weight % |
| --- | --- |
| EDTA, tetrasodium | 2.08 |
| EDTA, disodium | 1.92 |
| Preservative | q.s. |
| Deionized water to 100% | q.s. |
| pH 7.4 | |

Thus, an admixture of one part by weight of chelating composition (B) with 8 parts by weight soft water was delivered as a dilute chelating rinse (SB) spray containing a total of about 0.44% chelating agent (about 0.231% EDTA, tetrasodium salt and about 0.213% EDTA disodium salt).

The results are shown in Table 5 along with the calculated % inhibition in retaining Ca relative to that of the tap water rinsed tress control (A).

TABLE 5

| Tress | Rinse | Ca (mg/kg) | % Inhibition |
| --- | --- | --- | --- |
| A | Tap water | 10,171 | |
| B | Soft water | 2,309 | 77 |
| C | Chelating SA (Note 1) | 1,746 | 83 |
| D | Chelating SB (Note 2) | 1,597 | 84 |

Note 1: Admixture of soft water and Chelating Composition SA (Table 2)
Note 2: Admixture of Chelating Composition SB, (Table 4)

Surprisingly, the results showed that the beneficial amelioration in Ca sorption and retention was substantially the same on tresses (C) and (D) indicating the effect achieved with the admixture rinse of soft water and Chelating Composition (SA) which contains a total chelating agent content of about 0.22 wt % was substantially optimized.

EXAMPLE 5

This comparative example illustrates the use of the inventive delivery system generally shown in FIG. 1 during a chemical relaxation process under practical salon conditions. Salon studies were performed employing five African-American female subjects having naturally curly hair in need of chemical relaxation. Each subject was given her choice of commercial alkaline chemical (i.e., lye-type or no-lye type) relaxer product, applied according to the manufacturers's instructions.

The beneficial effect of the inventive chelating rinse employing the delivery system was assessed in half-head studies to remove the chemical relaxer from the hair on one side of the head (Side A) by following the rinsing procedure of Example 3, Study Group I, Tress C and Study Group II, Tress C, with admixture (SA) (i.e., one part by weight Chelating Composition (A), diluted with eight parts by weight soft water (0.064 ppm Ca)), and removing the chemical relaxer from the hair on the opposite side (Side B) with Chicago tap water delivered along path 12d of conduit 12 to the sprayer 14. The chemical relaxer was removed by rinsing the hair for about 4–6 minutes.

The chemical relaxing process was completed by neutralizing the residual alkalinity on the hair by washing with the normalizing shampoo composition A of Example 1, rinsing the hair on side A with soft water and side B with the tap water for about 2–3 minutes. Following base neutralization, a commercial conditioner containing cationic conditioning agents (AFFIRM® 5 in 1 Reconstructor, Avlon Industries, Inc.) was applied to the hair on both sides A and B and after about 1–2 minutes contact, the conditioned hair on side A and on side B was rinsed for about 2–3 minutes using soft water on side A and tap water on side B. Thus at all times soft water was employed on Side A and tap water was employed on side B.

The visual and tactile aesthetic attributes of the alkaline, relaxed hair were assessed by the professional hair stylists following the removal of the chemical relaxer, and again after completion of the process while the hair was wet. As summarized below in Table 6, the improved aesthetic attributes on side A were discernable in the step following the removal of the chemical relaxer as well as at the completion of the chemical relaxing process.

TABLE 6

| | % Agreement on Evaluation | |
| --- | --- | --- |
| Aesthetic Attribute of Hair | More Pronounced Side A | No Diff Side A = Side B |
| Manageability | 100 | |
| Combing Ease | 60 | 40 |
| Softness/smoothness | 100 | |
| Moisture | 80 | 20 |
| Lighter/More mobility | 100 | |
| Sheen | | 100 |

The results of the salon studies showed that, at all times, the use of the inventive delivery system to deliver the dilute soft water chelating rinse admixture containing a total of about 0.22 wt % chelating agent produced a discernible enhancement in the aesthetic attributes of the alkaline, relaxed hair.

EXAMPLE 6

This Example illustrates that the beneficial ameliorating effect of the inventive delivery system on inhibiting Ca sorption and retention can be achieved and even enhanced when post-relaxer conditioners are employed.

A series of naturally curly tresses were prepared as described in Example 1. The chemical relaxer procedure of Example 3, Study Group I, Tress C and Study Group II, Tress C was repeated, except that after removing the chemical relaxer, each tress was further conditioned by applying about 1–2 g of a commercial hair conditioner having a pH of about 4.5 and containing cationic conditioners, (Avlon Affirm® 5-in-1 Reconstructor, Avlon Industries, Inc.) The conditioner was left on the hair for about 1–2 minutes, then rinsed from the hair with soft water. The conditioning step was then followed by washing the conditioned hair once with the normalizing Shampoo Composition A of Example 1, to neutralize any remaining alkalinity on the hair, and then rinsing with soft water (Tress C/S in each Group).

For comparison, a second similar series of tresses were chemically relaxed following the relaxer procedure of Example 3, Study Group I, Tress A and Study Group II Tress A, except that following removal of the chemical relaxer, each tress was conditioned, as above, rinsed with tap water shampooed as described above and then rinsed with tap water (Tress C/T in each Group). The results are shown in Table 7 with the calculated inhibition on the C/S tress relative to the C/T tress in each group attributed to the use of the inventive delivery system.

TABLE 7

| Study Group | Tress | Ca (mg/kg) | % Inhibition |
|---|---|---|---|
| I | C/S | 1,150 | 79 |
| I | A/T | 5,480 | |
| II | C/S | 1,717 | 77 |
| II | C/T | 7,400 | |

EXAMPLE 7

This example illustrates the beneficial amelioration of Ca sorption and retention on chemically relaxed hair by employing wet wipes impregnated with the chelating composition (A) of Example 3 during a chemical relaxer process.

A series of impregnated wet chelating wipes in the form of towelettes were prepared. Each wet chelating wipe measured about 8×11 inches (about 20×28 centimeters) and was prepared employing paper crepe (23# weight). The paper crepe was impregnated with the Chelating Composition (A) of Example 3 and then folded and stored in a moisture impermeable packet measuring about 2⅜×3 inch until opened for use.

Useful wipes can be prepared employing a sheet:bath weight-ratio of about 1:2.1. Employing this ratio, a wipe having a dry weight of about 2.12 g, impregnated with about 4.4 g of the Chelating Composition (A) of Example 3 provided a wipe having a wet weight of about 6.52 g containing about 0.089 g of metal ion chelating agent.

A series of tresses of naturally curly hair were chemically relaxed for about 18 minutes employing the commercial no-lye type chemical relaxer, AFFIRM® Sensitive Scalp (SS) relaxer for resistant hair (Avlon Industries, Inc.). The relaxer was prepared for use and applied as described in Example 2, Table 1, Note 2, except that the chemical relaxer was removed from each tress by one of the following procedures, (A), (B), (C) or (D) as indicated in Table 8.

Procedure (A)

Step 1. The chemical relaxer was removed from the tress by rinsing with deionized water for at least about two to about three minutes;

Step 2. The rinsed tress was conditioned with the commercial conditioner of Example 6 following the conditioning procedure of Example 6;

Step 3. The conditioned tress was rinsed with deionized water for about two to about three minutes;

Step 4. The rinsed conditioned tress was shampooed once with the Shampoo Composition A of Example 1 to remove residual alkalinity from the hair;

Step 5. The shampooed tress was rinsed with deionized water for about two to about three minutes;

Step 6. The rinsed, shampooed tress was gently wiped with an impregnated chelating wet wipe, for about 1 minute and then towel blotted; and Step 7. The tress was analyzed for total Ca by the procedure of Example 1.

Procedure (B): Steps 1–7 of Procedure (A) were repeated, except that soft water (0.064 ppm Ca) was employed in rinse Steps 1, 3 and 5.

Procedure (C): Steps 1–7 of Procedure (A) were repeated, except that slightly hard tap water (about 37 ppm Ca) was employed in rinse Steps 1, 3 and 5.

Procedure (D): The relaxer was removed by rinsing with slightly hard tap water (about 37 ppm Ca), and the tress then analyzed for total Ca. This tress provided a comparative unwiped tap water control.

The results are shown in Table 8 along with the calculated % inhibition attributed to the use of the inventive wipe.

TABLE 8

| Proc. | Rinse Water | Ca (mg/kg) | % Inhibition |
|---|---|---|---|
| A | Deionized | 827 | 89 |
| B | Soft | 1,041 | 87 |
| C | Tap | 3,916 | 50 |
| D | Unwiped tap water control | 7,831 | |

The results show that employing the combination of the impregnated wet wipe and soft water rinse (Proc. B) inhibited the retention of Ca by the relaxed hair to the same degree as the combination of the impregnated wipe and deionized water rinse (Proc. A). Additionally, the hair was judged softer, lighter, and shinier then the hair treated by Procedure C. Some amelioration in Ca retention was achieved by the wet wipe in the presence of the slightly hard tap water rinse (Proc. C), but the beneficial result was substantially less than that achieved with the soft or deionized water. Thus, the intervening conditioning step did not interfere with the effectiveness of the wet wipes.

EXAMPLE 8

This example further illustrates the beneficial amelioration of Ca sorption and retention on chemically relaxed hair by employing wipes. The chemical relaxer procedure of Example 7 was repeated employing the deionized water rinse Procedure (A) and the tap water rinse Procedure (C), except that the wet wipes employed in step 6 of each procedure were impregnated with Chelating Composition (C) shown in Table 9. Composition C contained two conditioners.

TABLE 9

CHELATING COMPOSITION C

| Ingredient | Weight % (As Supplied) |
|---|---|
| EDTA, tetrasodium | 2.02 |
| Dimethicone bisamino hydroxypropyl copolyol (Note 3) | 1.11 |

TABLE 9-continued

CHELATING COMPOSITION C

| Ingredient | Weight % (As Supplied) |
|---|---|
| Polyquaternium-10 (Note 4) | 0.03 |
| Citric acid (to pH) | 0.3 |
| Deionized water to 100% | q.s. |
| pH 7.2 | |

Note 3: INCI name for SILSOFT A-843, sold as a 30% active solution by WITCO Corporation.
Note 4: INCI name for polymeric quaternary ammonium salt of hydroxyethyl cellulose reacted with a trimethyl ammonium substituted epoxide sold in varying molecular weights under the name UCARE Polymer JR by Amerchol Corporation, Edison, NJ. Preferred is UCARE Polymer JR 30M.

The results are shown in Table 10 together with the calculated % inhibition attributed to the use of the inventive wet wipes, compared to that of the unwiped tap water control of Example 7 (Proc. D).

TABLE 10

| Proc. | Rinse Water | Ca (mg/kg) | % Inhibition |
|---|---|---|---|
| A | Deionized | 1,195 | 85 |
| C | Tap | 3,702 | 53 |
| D | Unwiped Tap water control (Ex 7) | 7,831 | |

The results show that the combination of the impregnated wet wipe and deionized rinse water (Proc. A) ameliorated the retention of calcium by the relaxed hair to a greater extent than that achieved by the wet wipe in the presence of slightly hard tap rinse water (Proc. C). Additionally, the attributes of the hair following Procedure A, were judged softer, lighter and shinier than the attributes of hair following Procedure C.

EXAMPLE 9

This example illustrates the amelioration of sorption and retention of Ca on chemically relaxed hair by employing the chelating compositions of this invention in the form of a rinse.

On one tress (Tress A/A), the relaxer procedure of Example 7 was repeated employing the deionized water rinse Procedure (A), except that in Step 6, the hair was rinsed with about 2–3 g of the Chelating Composition (A) of Example 3. On a second tress (Tress A/C), the relaxer procedure of Example 7 was repeated employing the deionized water rinse Procedure (A), except that in Step 6, the hair was rinsed with about 2–3 g of Chelating Composition (C) of Example 8. On a third tress (Tress B/A), the relaxer procedure of Example 7 was repeated employing the soft water rinse Procedure (B), except that in Step 6, the hair was rinsed with about 2–3 g of Chelating Composition (A) of Example 3.

The results are shown in Table 11 along with the calculated % inhibition attributed to the use of the inventive rinses, compared to that of the tap water rinse control of Example 7, Procedure D (Tress D).

TABLE 11

| Proc. | Rinse Water | Ca (mg/kg) | % Inhibition |
|---|---|---|---|
| A/A | Deionized | 1,011 | 87 |
| A/C | Deionized | 1,072 | 86 |
| B/A | Soft | 1,103 | 86 |
| D | Tap, control (Ex. 7) | 7,831 | |

The data show that the Chelating Compositions A and C employed as rinses substantially inhibited the retention of calcium by the chemically relaxed hair.

EXAMPLE 10

This example illustrates the inhibition of Ca and Mg retention on alkaline, chemically relaxed hair by multiple applications of the inventive chelating wet wipe. An impregnated chelating wet wipe was prepared by dipping a paper crepe towel (23# weight) into about 2–3 g of Chelating Composition (D) having the formula shown in Table 12.

TABLE 12

CHELATING COMPOSITION D

| Ingredient | Active Weight % |
|---|---|
| EDTA, tetrasodium | 4 |
| Citric acid (to pH) | 0.58 |
| Deionized water to 100% | q.s. |
| pH 7.8 | |

A tress of naturally curly hair was chemically relaxed with the commercial no-lye type chemical relaxer (SS) of Example 2, prepared and used as in Note 2, Table 1 Example 2. The tap water rinsed alkaline, chemically relaxed hair was then substantially immediately gently wiped several times from the scalp portion down to the tip portion with the chelating wet wipe and then blotted with a cloth towel. The hair was then analyzed for total Ca and total Mg by the procedure of Example 1.

For comparison, a control tress was similarly chemically relaxed with the commercial no-lye type chemical relaxer prepared and used as described in Note 2, Table 1 of Example 2, but was unwiped. The results and calculated % inhibition of the retention of Ca and Mg and attributable to the wet wipe are shown in Table 13.

TABLE 13

| | (mg/kg) | | % Inhibition | |
|---|---|---|---|---|
| Tress | Ca | Mg | Ca | Mg |
| Twice wet wiped | 4,750 | 660 | 53 | 65 |
| Control (unwiped) | 10,200 | 1,880 | | |

When the wet wipe was employed with human subjects, minimal scalp irritation was noted since minimal scalp contact with the wet wipe occurs. Potential scalp irritation was further minimized by lowering the concentration of the chelating agent to about 2% in the impregnating composition without losing efficacy.

EXAMPLE 11

This example illustrates the inhibition of Ca and Mg retention on relaxed hair by multiple applications of the metal ion chelating compositions manually applied from pump sprays.

One tress(E) of naturally curly hair was chemically relaxed following the procedure of Example 2, with the commercial no-lye type chemical relaxer prepared and used as in Note 2, Table 1. The tap water rinsed alkaline, chemically relaxed hair was then substantially immediately manually sprayed once employing a hand held pump spray bottle containing Chelating Composition (E) having the formula shown in Table 14. The hair was sprayed from a distance of about 3 inches and sufficient spray was applied (about 2–3 g) to saturate the hair. The sprayed hair was then gently blotted with a cloth towel, sprayed a second time with Chelating Composition (E), and then blotted again with a cloth towel. The hair was then analyzed for total Ca and total Mg by the procedure of Example 1.

TABLE 14

CHELATING COMPOSITION E

| Ingredient | Active Weight % |
| --- | --- |
| EDTA, tetrasodium | 4 |
| Polyquaternium-10 (Note 4, Table 9) | 0.26 |
| Citric acid (to pH) | 0.55 |
| Deionized water to 100% | q.s. |
| pH 8.1 | |

A second Tress (C) of naturally curly hair was similarly chemically relaxed except that following the removal of the chemical relaxer, the tress was conditioned by applying about 1–2 g commercial conditioner, (Affirm® 5-in-1 Reconstructor), lathered and left on the hair for about 1–2 minutes, rinsed with slightly hard tap water (37 ppm Ca), shampooed with Shampoo Composition A of Example 1, rinsed with slightly hard tap water (37 ppm Ca); sprayed with Chelating Composition (C), Table 9, of Example 8, blotted with a cloth towel, sprayed a second time with Chelating Composition (C) and then blotted again with a cloth towel. The hair was then analyzed for total Ca and Mg by the procedure of Example 1.

The results are shown in Table 15 along with the calculated % inhibition of CA and Mg compared to the control of Example 10.

TABLE 15

| Tress | (mg/kg) | | % Inhibition | |
| --- | --- | --- | --- | --- |
| | Ca | Mg | Ca | Mg |
| Twice sprayed E | 5,550 | 785 | 46 | 58 |
| Twice sprayed C | 3,820 | 500 | 63 | 73 |
| Control (Ex. 10) | 10,200 | 1,880 | | |

When Chelating Composition (E), was pump sprayed onto the hair of a human subject immediately following a chemical relaxer treatment, scalp irritation was noted. The data again illustrate that the efficacy of the Chelating Composition (C) was greater than that of Chelating Composition (E).

EXAMPLE 12

The chemical relaxer and multiple manual spray procedure for tress E of Example 11 was repeated for a series of naturally curly hair tresses, except that the chelating spray employed on each separate tress was either Chelating Composition (F), (G), (H) or (I) as indicated in Tables 16 and 17.

TABLE 16

Chelating Compositions F, G, H, I

| Ingredient | Active Weight % | | | |
| --- | --- | --- | --- | --- |
| | F | G | H | I |
| EDTA tetrasodium | 1.06 | 2 | 3 | 4 |
| Citric Acid (to pH) | 0.16 | 0.31 | 0.46 | 0.58 |
| Deionized Water to 100% | q.s. | q.s | q.s. | q.s. |
| pH | 7.3 | 7.2 | 7.2 | 7.8 |

The total Ca and Mg content of the chemically relaxed tresses was analyzed and is shown in Table 17 compared to that of the control chemically relaxed, tap water rinsed tress of Example 10, together with the calculated % inhibition.

TABLE 17

| Sprayed | (mg/kg) | | % Inhibition | |
| --- | --- | --- | --- | --- |
| Tress | Ca | Mg | Ca | Mg |
| F | 6,750 | 1,730 | 34 | 8 |
| G | 4,650 | 1,240 | 54 | 34 |
| H | 3,600 | 1,125 | 65 | 40 |
| I | 5,350 | 860 | 48 | 54 |
| None (Ex. 10 Control) | 10,200 | 1,880 | | |

The results show that inhibition of Mg increased as the concentration of chelating agent increased to about 4% (I) whereas the inhibition of Ca was maximized at a concentration of about 3% chelating agent (H).

However, when the Chelating Composition (H) was similarly spray applied in salon studies to the hair of volunteer subjects having just received a chemical relaxer treatment, some irritation of the scalp was reported. Thus, the chelating spray preferably contains not more than about 3% total chelating agent.

EXAMPLE 13

This comparative example illustrates two commercial products reportedly containing chelating agents.

In one test, a commercial product was employed which was sold for use on dry hair as a pre-shampoo chelating treatment under the name Senscience® Complete Clarifier by Senscience International Dist., Division Zotos Corporation, Darien, Conn. The ingredients listed on the label are Deionized water, Trisodium EDTA, Sodium thiosulfate, Oleth-20, Soy Protein, Lecithin, Fragrance, Sodium hydroxymethylglycinate. The measurable pH of the product was about 9.4.

One tress(S/D) of naturally curly hair was chemically relaxed for about 18 minutes employing a commercial no-lye type chemical relaxer, AFFIRM® Sensitive Scalp (SS) relaxer (Avlon Industries, Inc.), Resistant Strength. The relaxer was prepared for use and applied as described in Example 2, Table 1, Note 2 and then dried overnight. The commercial product was then applied to the hair according to the manufacturer's instructions: "Spray Complete Clarifier on dry hair thoroughly saturating hair. Leave on for 3 minutes. Shampoo."

The shampoo employed for this study was Shampoo Composition (A) of Example 1, applied once and then rinsed with slightly hard tap water (about 37 ppm Ca) and the total Ca and Mg content of the tresses was then analyzed by the procedure of Example 1.

For comparison the procedure was repeated on a second tress (S/M) except that following the removal of the chemical relaxer, the alkaline, chemically relaxed hair was towel dried to remove excess moisture so that the tress was still moist when the product was sprayed on.

In a second test, a commercial "decalciumfier" conditioner product was employed which is sold under the name After Calcium by Request Products, Orlando, Fla. for use on the hair and scalp. The product is promoted as being "designed to be used after all calcium relaxers and no base relaxers" and as being a "unique blend of 8 conditioners" which among other benefits "help cut down on calcium buildup." The ingredients listed on the label are: "Deionized Water, Mineral Oil, Polyquaternium 32(and)Mineral Oil, Glycerine, Stearalkonium Chloride, Silicone, Fragrance, Hydrolyzed Wheat Protein, Tetrasodium EDTA, Jojoba Oil, Aloe Vera Oil, Silk Amino Acids, Propylene Glycol(and) Diazolidinyl Urea(and)Methylparaben(and)Propylparaben." The measurable pH of the product was 4.3.

For this test, a third 2 gram tress (AC) of naturally curly hair was prepared and then chemically relaxed with the commercial no-lye type chemical relaxer as described above. After removing the relaxer by rinsing the hair thoroughly, the hair was towel dried and about 6 grams of the After Calcium product was applied to the 2 g tress according to the manufacturer's instructions. The product was combed through the hair thoroughly and left in contact with the hair for 5 minutes, rinsed from the tress, then reapplied to the tress and left in contact with the hair for about 5–10 minutes and then rinsed from the hair. The total Ca and Mg content of the tress was then analyzed by the procedure of Example 1.

The results are shown in Table 18 together with the calculated % inhibition compared to the chemically relaxed control of Example 10.

TABLE 18

| Tress | (mg/kg) | | % Inhibition | |
| --- | --- | --- | --- | --- |
|  | Ca | Mg | Ca | Mg |
| S/D | 7,870 | 1,515 | 23 | 19 |
| S/M | 9,435 | 2,080 | 8 | −11 |
| AC | 8,050 | 1,200 | 21 | 36 |
| Control (Ex. 10) | 10,200 | 1,880 |  |  |

The results show that the commercial Senscience® product was not effective in removing Ca from the moist alkaline, chemically relaxed hair (S/M) and increased the total Mg content. Additionally, the tresses were dull and heavy (coated). Thus, unlike the present inventive chelating compositions, the Senscience product is limited to preshampoo use on dry hair (S/D). The commercial After Calcium product was more effective than the Senscience® product but the tress (AC) had a heavy feel (i.e. dull and coated) and hair attributes (i.e. manageability, mobility, moisture softness) were judged less than achieved by the practice of this invention.

EXAMPLE 14

This comparative example illustrates the surprising chelation efficacy of Chelating Composition A, of Example 3 over that of commercial chelating compositions described in Examples 2 and 13 as shown in Table 19 below together with their calculated chelation value. The calculated chelation value was determined as follows and provides an estimate of combined efficacy of all the metal ion chelating agents present in the test sample:

1. A test sample (4 g) was weighed into a 250 ml Erlenmeyer flask;
2. Deionized water (80 ml) and a 3% ammonium oxalate solution (10 ml) were added to the contents of the flask and stirred to disperse the test sample completely;
3. The resultant test mixture was then titrated with aqueous calcium chloride solution (0.25M) until permanent turbidity first appeared;
4. The pH of the turbid mixture was adjusted to a value above pH 11 with aqueous sodium hydroxide (1N);
5. If turbidity cleared, titration with calcium chloride solution was continued until permanent turbidity re-occurred;
6. The volume (ml) of calcium chloride solution used was recorded; and
7. The chelation value (mg/g) was calculated as:

$$\frac{(\text{ml of calcium chloride})(\text{Molarity of calcium chloride})(100)}{\text{Sample weight in g.}}$$

TABLE 19

| Test Sample | Initial pH of Test Sample | Chelation Value (mg/g) |
| --- | --- | --- |
| Chelating Composition A, Ex. 3 | 7.4 | 5.5 |
| L'AVANTGARDE Clean Canvas, Ex. 2 | 7.7 | 14.2 |
| Senscience ® Complete Clarifier, Ex. 13 | 9.4 | 6.5 |
| After Calcium, Ex. 13 | 4.3 | 12.2 |

Chelating Composition A of Example 3 had the lowest calculated chelation value, yet surprisingly it was more effective at inhibiting Ca retention than the commercial products as illustrated in the foregoing Examples 2, 3 and 13.

EXAMPLE 15

This comparative example illustrates the exacerbated retention of 11 exogenous multivalent metal ions by alkaline chemically relaxed hair when slightly hard tap water (Lake Michigan) was employed as the rinse water instead of soft water, where the total multivalent metal concentration of the rinse waters was as shown in the Chart of Example 1.

One set (Group I) of naturally curly African-American hair tresses was prepared as described in Example 1, except that the hair was used as supplied, and then chemically relaxed with the commercial organic base (no-lye type) chemical relaxer for resistant hair, AFFIRM® Sensitive Scalp relaxer (SS) (Avlon Industries, Inc.), prepared for use and applied to the hair as described in Note 2, Table 1 of Example 2 and was left in contact with the hair for about 18 minutes. The chemical relaxer was then removed from the alkaline chemically relaxed hair by rinsing for about three minutes with either tap water (Tress I-TW) or with soft water (Tress I-SW).

A second set (Group II) of tresses was similarly prepared, except that the tresses were chemically relaxed with the commercial chemical relaxer containing about 2.2% sodium hydroxide, AFFIRM®, resistant strength (Avlon Industries, Inc.), applied to the hair as described in Example 3, and left in contact with the hair for about 18 minutes. The chemical relaxer was then removed from the alkaline chemically relaxed hair by rinsing for about three minutes with either tap water (Tress II-TW) or soft water (Tress II-SW).

The total concentration in mg/kg of 11 multivalent metal ions found in the alkaline chemically relaxed tresses in each of the groups was then determined by ICP technique. The results are shown below in Table 20 together with the times increase of metal ion sorption by tap water rinsed hair over the soft water rinsed hair.

TABLE 20

Total Metal Ion Concentration (mg/kg)

| Tress | Alkaline Earth Metal | | | | Transition Metal | | | | Heavy Metal | | |
| --- | --- | --- | --- | --- | --- | --- | --- | --- | --- | --- | --- |
| | Ba | Ca | Mg | Sr | Cu | Fe | Mn | Ni | Al | Pb | Zn |
| I-SW | 3 | 2207 | 226 | 5 | 7 | 24 | 18 | 17 | 50 | 51 | 133 |
| I-TW | 7 | 7824 | 1806 | 24 | 72 | 31 | 30 | 54 | 60 | 107 | 181 |
| Times Increase | 2.3 | 3.5 | 7.99 | 4.8 | 10.28 | 1.29 | 1.11 | 2 | 1.2 | 2.1 | 1.36 |
| II-SW | 3 | 1842 | 226 | 7 | 16 | 2 | 7 | 35 | 60 | 44 | 90 |
| II-TW | 6 | 6825 | 1657 | 21 | 64 | 3 | 8 | 62 | 68 | 56 | 144 |
| Times Increase | 2 | 3.7 | 7.33 | 3 | 4 | 1.5 | 1.14 | 1.77 | 1.13 | 1.27 | 1.6 |

The data show that, regardless of relaxer type employed, tap water rinsing permitted the total content of each exogenous multivalent metal ion in the chemically-relaxed hair to increase more than 1.1 fold, with the most increased being alkaline earth metal ions and copper which increased more than 2 fold.

EXAMPLE 16

This example illustrates the surprising effectiveness of employing the inventive delivery system to concurrently remove the chemical relaxer from the alkaline chemically-relaxed hair while inhibiting the retention of multivalent metal ion by delivering a dilute admixture of soft water and metal ion chelating composition containing less than about 0.5% chelating agent.

One tress (I-A/SW) was prepared and relaxed with the commercial no-lye type relaxer and procedure of Example 15 for the Group I tresses, except that the chemical relaxer was removed from the hair employing about a three minute rinse of an admixture of one part by weight of the Chelating Composition (A) of Example 3 with eight parts by weight of soft water delivered to the hair employing the inventive delivery system as described in Example 3.

A second tress (II-A/SW) was prepared and relaxed with the commercial lye-type relaxer and the procedure of Example 15 for the Group II tresses, except that the chemical relaxer was removed from the hair employing about a three minute rinse of an admixture of one part by weight of the Chelating Composition (A) of Example 3 with eight parts by weight of soft water delivered to the hair employing the inventive delivery system as described in Example 3.

A third tress (II-B/SW) was relaxed with the commercial no-lye type relaxer and the procedure of Example 15 for the Group I tresses, except that the chemical relaxer was removed from the hair employing about a three minute rinse of an admixture of one part by weight of the Chelating Composition (B) of Example 4 with eight parts by weight of soft water delivered to the hair employing the inventive delivery system as described in Example 3.

The total concentration (mg/kg) was determined as in Example 15 for the 11 selected multivalent metal ions in the I-A/SW tress and for eight selected metal ions in the I-B/SW and II-B/SW tresses. The data are shown in Table 21 together with the % inhibition compared to the total metal ion concentration of Group I-TW and Group II-TW set of tresses from Example 15.

TABLE 21

Total Metal Ion Concentration (mg/kg)

| Tress | Ba | Ca | Mg | Sr | Cu | Fe | Mn | Ni | Al | Pb | Zn |
| --- | --- | --- | --- | --- | --- | --- | --- | --- | --- | --- | --- |
| I-TW (Ex. 15) | 7 | 7824 | 1806 | 24 | 72 | 31 | 20 | 54 | 60 | 107 | 181 |
| I-A/SW | 2 | 1172 | 178 | 2 | 10 | 7 | 17 | 2 | 0 | 0 | 87 |
| % Inhibition | 71 | 85 | 90 | 92 | 86 | 77 | 15 | 96 | 100 | 100 | 52 |
| II-TW (Ex. 15) | 6 | 6825 | 1657 | 31 | 64 | 3 | 8 | 62 | 68 | 56 | 144 |
| II-A/SW | 2 | 1245 | 179 | 4 | 17 | n.a. | n.a. | 1 | n.a. | 35 | 78 |
| % Inhibition | 67 | 82 | 89 | 81 | 73 | | | 98 | | 38 | 46 |
| II B/SW | 2 | 1140 | 163 | 3 | 19 | n.a. | n.a. | 0 | n.a. | 4 | 83 |
| % Inhibition | 67 | 83 | 90 | 86 | 70 | | | 100 | | 93 | 42 | n.a. = not analyzed

The data illustrate the surprising effectiveness of the dilute admixture of chelating rinse and soft water employing the delivery system in inhibiting the retention of multivalent metal ion by alkaline chemically relaxed hair, regardless of relaxer type. The % inhibition achieved with the diluted admixture of Chelating Composition (A) containing a total of about 0.22% chelating agents was judged substantially maximized for all the metal ions, except for Pb on alkali hydroxide relaxed hair (II-A/SW), which was inhibited to a greater extent by the diluted admixture of Chelating Composition (B) containing a total of 0.44% chelating agents.

EXAMPLE 17

This example illustrates the efficacy of employing impregnated chelating wipes prepared and provided in substantially dry form, which are re-moistened with water just before use.

One impregnated chelating wipe (A) was prepared by dipping a paper crepe towel (23# weight) into about 2–3 g of Chelating Composition (A) of Example 3, Table 2. The saturated substrate was then substantially dried at 70° C. A second impregnated substantially dry chelating wipe (B) was similarly prepared, except that Chelating Composition (B) of Example 4, Table 4 was employed. For use, the substantially dry wipes were re-moistened by spraying with sufficient deionized water to uniformly wet the wipe substrate without dripping.

Tresses of naturally curly hair were prepared as described in Example 1, except that the hair was used as supplied, and the tresses were chemically relaxed with commercial chemical relaxer containing about 2.2% sodium hydroxide (AFFIRM®, resistant strength, Avlon Industries, Inc.) for about 18 minutes. The chemical relaxer was removed from the hair by rinsing with slightly hard tap water (Lake Michigan) having the multivalent metal ion concentration shown in the chart of Example 1 for about three minutes. One alkaline chemically relaxed tress was then wiped several times several times from the scalp portion downward to the tip portion with the re-moistened wipe (A) and a second alkaline chemically relaxed tress was similarly wiped with the re-moistened wipe (B). The tresses were then analyzed for total content of eight multivalent metal ions by ICP technique. The results are shown in Table 22 with % inhibition compared to the metal ion content of tap water rinsed, unwiped tresses II-TW of Example 15.

TABLE 22

| Tress | Total Metal Ion Concentration (mg/kg) | | | | | | | |
|---|---|---|---|---|---|---|---|---|
| | Ba | Ca | Mg | Sr | Cu | Ni | Al | Zn |
| II-TW (Ex. 15) | 6 | 6825 | 1657 | 21 | 64 | 62 | 68 | 144 |
| Wipe A | 5 | 3996 | 1169 | 13 | 51 | 27 | 62 | 97 |
| % Inhibition | 17 | 41 | 29 | 38 | 20 | 56 | 9 | 36 |
| Wipe B | 4 | 35 | 1147 | 13 | 35 | 27 | 62 | 94 |
| % Inhibition | 33 | 45 | 31 | 38 | 45 | 56 | 9 | 35 |

Overall the beneficial efficacy of the relaxer method of this invention was substantially unaffected by employing optional hair conditioning agents either in the chelating composition or by including a hair conditioning step intervening the removal of the chemical relaxer and the contact of the chelating composition with the chemically-relaxed hair during the relaxer process. The use of the inventive delivery system optimized the efficacy of the relaxer method of this invention and inhibiting efficacy of the chelating composition.

The present invention has been described generally and with respect to preferred embodiments. It will be understood that modifications and variations of the disclosed method, compositions and delivery system may be made without departing from the spirit and scope of the novel concept of the present invention.

We claim:

1. A method for ameliorating and inhibiting the adsorption and retention of exogenous multivalent metal ion by chemically-relaxed hair during the process of relaxing naturally curly hair with compositions containing chemical base, the method consisting of the sequential steps of:

(a) contacting naturally curly hair with a hair relaxing composition having a pH above about 12 and containing an effective hair-relaxing amount of chemical base for a period sufficient to relax all or a portion of the natural curl to provide alkaline, chemically-relaxed hair;

(b) removing the hair relaxing composition from the alkaline, chemically-relaxed hair by substantially immediately contacting the alkaline, chemically-relaxed hair for at least about two minutes with an aqueous metal ion chelating composition having a physiologically tolerable pH and containing an effective chelating amount of at least one exogenous multivalent metal ion chelating agent wherein the exogenous multivalent metal ion is a member of the group consisting of alkaline earth metal ions, transition metal ions, and heavy metal ions;

(c) optionally neutralizing residual alkalinity on the chemically-relaxed hair by contact the chemically-relaxed hair with an alkalinity neutralizing composition having a pH in the range of about 5 to about 7; and (d) optionally conditioning the chemically relaxed hair during step (b) or in a step prior to or after step (c).

2. The method of claim 1 wherein step (b) is performed by (i) first rinsing the alkaline chemically-relaxed hair with water having a hardness level of not more than 17 parts per million and (ii) substantially immediately thereafter contacting the water rinsed alkaline chemically-relaxed hair with the metal ion chelating composition.

3. The method of claim 2 wherein the rinse water has a hardness level of not more than about 1 part per million.

4. The method of claim 1 wherein the exogenous alkaline earth metal ion is selected from the group consisting of barium, calcium, magnesium and strontium; the exogenous transitional metal ion is selected from the group consisting of copper, iron, manganese and nickel; and the heavy metal ion is selected from the group consisting of aluminum, lead and zinc.

5. The method of claim 1 wherein the exogenous multivalent metal ion is at least one alkaline earth metal ion selected from the group consisting of calcium and magnesium.

6. The method of claim 1 wherein in step (b) the aqueous metal ion chelating composition contains a metal ion chelating agent selected from the group consisting of ethylenediaminetetraacetic acid, diethylenetriaminepentaacetic acid, hydroxyethylethylenediaminetriacetic acid, nitrilotriacetic acid, ethanol diglycine, ethylenebis(hydroxyphenylglycine), N-dihydroxyethylglycine, iminodisuccinic acid, ethylenediaminedisuccinic acid, polyaspartic acid, and water soluble alkali metal salts thereof, employed singly or in combination.

7. The method of claim 1 wherein the aqueous metal ion chelating composition in step (b) contains not more than about 0.5 weight percent of metal ion chelating agent.

8. The method of claim 2 wherein the aqueous metal ion chelating composition in step (b)(ii) contains not more than about 3 weight percent of metal ion chelating agent.

9. The method of claim 2 wherein in step (b)(ii) the contact is carried out with the metal ion chelating composition in the form of a liquid rinse or spray.

10. The method of claim 2 wherein in step (b)(ii) the contact is carried out employing a wipe comprising a fibrous, flexible sheet material previously impregnated with the aqueous metal ion chelating composition and wiping the hair directionally away from the scalp portion along the full length of the hair to its end portion.

11. The method of claim 10 wherein the impregnated wipe is provided in the form of a wet wipe.

12. The method of claim 10 wherein the impregnated wipe is provided in the form of a substantially dry wipe and is re-moistened with water for use.

13. The method of claim 10 wherein the impregnating aqueous metal ion chelating composition contains, on a total composition basis, alkaline earth metal ion chelating agent in an amount of not more than about 4.5 weight percent.

14. A method for ameliorating and inhibiting the adsorption and retention of exogenous multivalent metal ion by chemically-relaxed hair during the process of relaxing naturally curly hair with compositions containing chemical base, the method comprising the sequential steps of:

(a) contacting naturally curly hair with a hair relaxing composition having a pH above about 12 and containing an effective hair-relaxing amount of chemical base for a period sufficient to relax all or a portion of the natural curl to provide alkaline, chemically-relaxed hair; and (b) removing the hair relaxing composition from the alkaline, chemically-relaxed hair by substantially immediately contacting the alkaline, chemically-relaxed hair for at least about two minutes with an aqueous metal ion chelating composition having a physiologically tolerable pH and containing an effective chelating amount of at least one exogenous multivalent metal ion chelating agent wherein the exogenous multivalent metal ion is a member of the group consisting of alkaline earth metal ions, transition metal ions, and heavy metal ions;

wherein the aqueous metal ion chelating composition is delivered to the alkaline, chemically-relaxed hair from a delivery system comprising in combination:

a) a conduit having at least one water inlet being operably and changeably connected in liquid flow communication to a source of incoming raw water, at least one liquid outlet being operably and changeably connectable to a liquid sprayer and at least one injector intermediate the water inlet and the liquid outlet and sprayer, the injector further having an inlet being operably and changeably connectable in liquid flow communication to a source of aqueous metal ion chelating composition for concurrently receiving and admixing the received aqueous metal ion chelating composition with water flowing through the conduit;

b) a water softener intermediate the water inlet and the injector, and c) at least one valve located within the conduit being positionable and configured such that water flow through the conduit to the liquid outlet can be optionally channeled to:

i) pass through both the water softener and the injector for concurrently delivering an admixture of softened water having a hardness level of not more than 17 ppm and a predetermined amount of the aqueous metal ion chelating composition; or ii) pass through the injector, bypassing the water softener, for concurrently delivering an admixture of predetermined amount of the aqueous metal ion chelating composition and raw incoming water.

15. The method of claim 14 wherein the delivery system comprises a plurality of valves located within the conduit each valve being positionable and configured such that water flow through the conduit directly to the liquid outlet can be further optionally channeled to:

iii) pass through the water softener for delivery of softened water having a hardness level of not more than 17 ppm; or iv) deliver raw incoming water.

16. The method of claim 14 wherein the injector further includes a valve for controlling the amount of the aqueous metal ion chelating composition injected.

17. The method of claim 14 wherein the liquid outlet includes a liquid sprayer.

18. The method of claim 14 wherein the water delivered to the liquid outlet has a hardness level of not more than about 1 ppm.

19. The method of claim 14 wherein the injector is connected in liquid flow communication with a source of aqueous metal ion chelating composition comprising, prior to injection, on a total composition basis, not more than about 5 weight percent of at least one alkaline earth metal ion chelating agent and on injection is diluted on a weight to weight basis with water from about 1:1 to about 1:10 in the resulting admixture.

20. The method of claim 19 wherein, on injection, the resulting admixture contains not more than about 0.5 weight percent total metal ion chelating agent on a total admixture basis.

21. The method of claim 14 wherein the source of aqueous metal ion chelating composition comprises a metal ion chelating agent selected from the group consisting of ethylenediaminetetraacetic acid, diethylenetriaminepentaacetic acid, hydroxyethylethylenediaminetriacetic acid, nitrilotriacetic acid, ethanol diglycine, ethylenebis (hydroxyphenylglycine), N-dihydroxyethylglycine, iminodisuccinic acid, ethylenediaminedisuccinic acid, polyaspartic acid, and water soluble alkali metal salts thereof, employed singly or in combination.

22. The method of claim 14 wherein the delivery system further includes an injector being operably and changeable connectable for delivery of an admixture of water and liquid composition containing a conditioning agent.

23. A modular apparatus for concurrently delivering an admixture of water and aqueous metal ion chelating composition to alkaline chemically-relaxed hair for ameliorating and inhibiting the adsorption and retention of exogenous multivalent metal ion by chemically-relaxed hair during a process of relaxing naturally curly hair with a hair relaxing composition having a pH above about 12 and containing an effective hair-relaxing amount of chemical base for a period sufficient to relax all or a portion of the natural curl to provide alkaline, chemically-relaxed hair, wherein the hair relaxing composition is removed from the alkaline, chemically-relaxed hair by substantially immediately contacting the alkaline, chemically-relaxed hair for at least about two minutes with an aqueous metal ion chelating composition having a physiologically tolerable pH and containing an effective chelating amount of at least one exogenous multivalent metal ion chelating agent wherein the exogenous multivalent metal ion is a member of the group consisting of alkaline earth metal ions, transition metal ions, and heavy metal ions:

the apparatus comprising:

a) a conduit having at least one water inlet for being operably and changeably connectable to a source of incoming raw water, and at least one liquid outlet; and b) at least one injector positionable intermediate the water inlet and the liquid outlet of the conduit, the injector further having an inlet adapted for receiving aqueous metal ion chelating composition from a reservoir therefor for concurrently admixing the received aqueous metal ion chelating composition with water when water is flowing through the conduit.

24. The apparatus of claim 23 further including a water softener positionable intermediate the water inlet and the injector, and
   a) a plurality of valves locatable within the conduit, each valve positionable such that when water flows through the conduit to the liquid outlet, the water can be optionally channeled to:
      i) pass through both the water softener and the injector for concurrently delivering to the liquid outlet an admixture of softened water having a hardness level of not more than 17 ppm and a predetermined amount of the aqueous metal ion chelating composition; or
      ii) pass through the injector, bypassing the water softener, for concurrently delivering to the liquid outlet an admixture of predetermined amount of the aqueous metal ion chelating composition and raw incoming water.

25. The apparatus of claim 24 wherein each valve is further positionable such that water flow through the conduit to the liquid flow outlet can be optionally channeled to:
   iii) pass through the water softener for direct delivery of softened water having a hardness level of not more than 17 ppm to the liquid flow outlet; or
   iv) deliver raw incoming water to the liquid flow outlet.

26. The apparatus of claim 24 further including a meter for metering the delivery of softened water from the water softener tank to the liquid flow outlet.

27. The apparatus of claim 23 wherein the injector includes a valve for controlling the amount of received aqueous metal ion chelating composition.

28. The apparatus of claim 23 wherein the liquid flow outlet includes a liquid sprayer.

29. An article of manufacture comprising in packaged form the modular apparatus of claim 23.

30. The article of manufacture of claim 29 further including packaged therein a container comprising a liquid aqueous metal ion chelating composition.

31. The article of manufacture of claim 29 further including packaged therein at least one valve, positionable within the conduit for controlling the flow of water through the conduit to the liquid flow outlet.

32. The article of manufacture of claim 29 including packaged therein a liquid sprayer.

33. A liquid metal ion chelating composition for use in the method of claim 14 comprising in packaged form:
   about 1 to about 1.5 weight percent disodium salt of ethylenediaminetetraacetic acid;
   about 1 to about 1.5 weight percent tetrasodium salt of ethylenediaminetetraacetic acid; and
   the remainder being water and optional cosmetic adjuvants wherein the package is adapted for placing the contents thereof in liquid fluid flow communication with the injector.

34. An article of manufacture comprising an impregnated wipe useful for ameliorating and inhibiting the adsorption and retention of exogenous multivalent metal ion by chemically-relaxed hair during a process of relaxing naturally curly hair with a hair relaxing composition having a pH above about 12 and containing an effective hair-relaxing amount of chemical base for a period sufficient to relax all or a portion of the natural curl to provide alkaline, chemically-relaxed hair, wherein the hair relaxing composition is removed from the alkaline, chemically-relaxed hair, as by rinsing the alkaline chemically-relaxed hair with water having a hardness level of not more than 17 parts per million, and substantially immediately thereafter the water rinsed alkaline chemically-relaxed hair is contacted for at least about two minutes with the impregnated wipe;
   the wipe comprising a fibrous, flexible sheet material impregnated with an aqueous metal ion chelating composition having a physiologically tolerable pH and containing an effective chelating amount of at least one exogenous multivalent metal ion chelating agent, wherein the exogenous multivalent metal ion is a member of the group consisting of alkaline earth metal ions, transition metal ions, and heavy metal ions.

35. The impregnated wipe of claim 34 contained in a package.

* * * * *

UNITED STATES PATENT AND TRADEMARK OFFICE
CERTIFICATE OF CORRECTION

PATENT NO. : 6,602,493 B2
DATED : August 5, 2003
INVENTOR(S) : Humayoun Akhter and Ali N. Syed It is certified that error appears in the above-identified patent and that said Letters Patent is hereby corrected as shown below:

Column 14,
Line 60, delete "GYROTORYO®" and insert -- GYROTORY® --.

Column 21,
Line 48, delete "-" after "weight".

Columns 29 and 30,
Last line, delete
  "% Inhibition 67  83  90  86  70        100  93  42" and insert
-- % Inhibition 67  83  90  86  70        100      93  42 --

Signed and Sealed this

Sixteenth Day of December, 2003

JAMES E. ROGAN
*Director of the United States Patent and Trademark Office*